(12) United States Patent
Meyer et al.

(10) Patent No.: US 12,167,967 B2
(45) Date of Patent: *Dec. 17, 2024

(54) FLEXIBLE INTERBODY IMPLANT

(71) Applicant: K2M, Inc., Leesburg, VA (US)

(72) Inventors: Joseph Michael Meyer, Bethel, OH (US); Kevin Orbine, Bernardsville, NJ (US)

(73) Assignee: K2M, Inc., Leesburg, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/206,707

(22) Filed: Jun. 7, 2023

(65) Prior Publication Data

US 2023/0310173 A1 Oct. 5, 2023

Related U.S. Application Data

(63) Continuation of application No. 17/162,357, filed on Jan. 29, 2021, now Pat. No. 11,707,361.

(Continued)

(51) Int. Cl.
*A61F 2/44* (2006.01)
*A61F 2/30* (2006.01)

(52) U.S. Cl.
CPC .. *A61F 2/4465* (2013.01); *A61F 2002/30131* (2013.01); *A61F 2002/30133* (2013.01);
(Continued)

(58) Field of Classification Search
CPC .......... A61F 2/44; A61F 2/442; A61F 2/4425; A61F 2/4455; A61F 2/446; A61F 2/4465;
(Continued)

(56) References Cited

U.S. PATENT DOCUMENTS 6,136,031 A 10/2000 Middleton
6,206,923 B1 3/2001 Boyd et al.
(Continued)

FOREIGN PATENT DOCUMENTS

DE 19710392 C1 7/1999
EP 1925271 A1 5/2008
(Continued)

OTHER PUBLICATIONS

Papp, Donald, "Hackday: 3D Printing Flexible Surfaces out of Non-Flexible Material", Retrieved from the Internet https://hackaday.com/2017/08/05/3d-printing-flexible-surfaces-out-of-non-flexible-material/ <https://protect-us.mimecast.com/s/EsZvCwpRk5hGLQQ3iVfdT7?domain=hackaday.com>>, Aug. 5, 2017, 10 pages.

(Continued)

*Primary Examiner* — Eric S Gibson
(74) *Attorney, Agent, or Firm* — Lerner David LLP

(57) ABSTRACT

A lumbar interbody fusion device includes a first wing, a second wing, and a bridge. The bridge has an arcuate resting shape and include a first end connected to the first wing, a second end connected to the second wing, and at least one aperture extending through the bridge in a radial direction relative to the arcuate resting shape of the bridge. The bridge is elastically deformable such that a distance between the first wing and the second wing may vary according to elastic deformation of the bridge.

18 Claims, 18 Drawing Sheets

Related U.S. Application Data

(60) Provisional application No. 62/970,258, filed on Feb. 5, 2020.

(52) U.S. Cl.
CPC ............ *A61F 2002/30176* (2013.01); *A61F 2002/30291* (2013.01); *A61F 2002/30566* (2013.01); *A61F 2002/30571* (2013.01); *A61F 2002/30622* (2013.01); *A61F 2002/30937* (2013.01); *A61F 2002/30971* (2013.01); *A61F 2002/30985* (2013.01); *A61F 2310/00023* (2013.01)

(58) Field of Classification Search
CPC ............ A61F 2/447; A61F 2002/30971; A61F 2002/30985; A61F 2002/444; A61F 2310/00023
See application file for complete search history.

(56) References Cited

U.S. PATENT DOCUMENTS

| | | | |
|---|---|---|---|
| 6,387,130 B1 * | 5/2002 | Stone | A61F 2/4611 623/17.16 |
| 6,833,006 B2 | 12/2004 | Foley et al. | |
| 7,125,424 B2 | 10/2006 | Banick et al. | |
| 7,520,900 B2 | 4/2009 | Trieu | |
| 7,537,664 B2 | 5/2009 | O'Neill et al. | |
| 7,789,914 B2 | 9/2010 | Michelson | |
| 8,016,829 B2 | 9/2011 | Mahoney et al. | |
| 8,021,429 B2 | 9/2011 | Viker | |
| 8,034,110 B2 * | 10/2011 | Garner | A61F 2/4611 623/17.11 |
| 8,142,507 B2 | 3/2012 | McGuckin, Jr. | |
| 8,147,861 B2 | 4/2012 | Jones et al. | |
| 8,350,186 B2 | 1/2013 | Jones et al. | |
| 8,728,387 B2 | 5/2014 | Jones et al. | |
| 8,828,082 B2 * | 9/2014 | Puno | A61F 2/4611 623/17.11 |
| 8,882,841 B2 * | 11/2014 | Falahee | A61F 2/4455 623/17.16 |
| 8,992,620 B2 | 3/2015 | Ashley et al. | |
| 8,992,703 B2 | 3/2015 | O'Neill et al. | |
| 9,044,333 B2 * | 6/2015 | Puno | A61F 2/4455 |
| 9,044,334 B2 | 6/2015 | Siegal et al. | |
| 9,119,729 B2 | 9/2015 | Falahee | |
| 9,135,374 B2 | 9/2015 | Jones et al. | |
| 9,180,010 B2 | 11/2015 | Dong et al. | |
| 9,320,614 B2 | 4/2016 | Garner et al. | |
| 9,456,901 B2 | 10/2016 | Jones et al. | |
| 9,814,599 B2 * | 11/2017 | Puno | A61F 2/4611 |
| 9,844,443 B2 * | 12/2017 | Puno | A61F 2/4684 |
| 9,877,844 B2 * | 1/2018 | Puno | A61F 2/4611 |
| 10,130,486 B2 * | 11/2018 | Puno | A61F 2/442 |
| 10,806,594 B2 * | 10/2020 | Puno | A61F 2/4611 |
| 10,835,386 B2 * | 11/2020 | Puno | A61F 2/4611 |
| 11,707,361 B2 * | 7/2023 | Meyer | A61F 2/4465 623/17.11 |
| 2005/0119747 A1 | 6/2005 | Fabris Monterumici et al. | |
| 2006/0041258 A1 | 2/2006 | Galea | |
| 2006/0147332 A1 | 7/2006 | Jones et al. | |
| 2007/0067035 A1 * | 3/2007 | Falahee | A61F 2/4611 623/17.11 |
| 2007/0073398 A1 | 3/2007 | Fabian et al. | |
| 2007/0260314 A1 * | 11/2007 | Biyani | A61F 2/4611 623/17.11 |
| 2007/0260324 A1 | 11/2007 | Joshi et al. | |
| 2008/0058933 A1 * | 3/2008 | Garner | A61F 2/442 623/17.11 |
| 2008/0125865 A1 * | 5/2008 | Abdelgany | A61F 2/4611 623/17.11 |
| 2008/0234687 A1 | 9/2008 | Schaller et al. | |
| 2008/0234827 A1 | 9/2008 | Schaller et al. | |
| 2008/0243255 A1 | 10/2008 | Butler et al. | |
| 2008/0249628 A1 * | 10/2008 | Altarac | A61F 2/4455 623/17.11 |
| 2008/0312743 A1 | 12/2008 | Vila et al. | |
| 2009/0143859 A1 | 6/2009 | McClellan, III et al. | |
| 2009/0182431 A1 | 7/2009 | Butler et al. | |
| 2014/0114414 A1 | 4/2014 | Abdou et al. | |
| 2014/0277486 A1 | 9/2014 | Abdou et al. | |
| 2014/0358246 A1 * | 12/2014 | Levy | A61F 2/4455 623/23.47 |
| 2017/0156880 A1 * | 6/2017 | Halverson | A61F 2/4455 |
| 2017/0290671 A1 | 10/2017 | Milz et al. | |
| 2018/0064558 A1 * | 3/2018 | Puno | A61F 2/4611 |
| 2018/0133026 A1 * | 5/2018 | Puno | A61F 2/4611 |
| 2018/0338842 A1 | 11/2018 | Garner et al. | |
| 2019/0070014 A1 * | 3/2019 | Puno | A61F 2/4611 |
| 2019/0133783 A1 | 5/2019 | Unger et al. | |
| 2019/0343644 A1 | 11/2019 | Ryan et al. | |
| 2019/0343651 A1 * | 11/2019 | Ryan | A61F 2/4455 |
| 2021/0236300 A1 * | 8/2021 | Meyer | A61F 2/4465 |
| 2023/0310173 A1 * | 10/2023 | Meyer | A61F 2/4465 623/17.11 |

FOREIGN PATENT DOCUMENTS

| | | |
|---|---|---|
| EP | 2967901 A1 | 1/2016 |
| FR | 2900814 A1 | 11/2007 |
| WO | 2014144696 A1 | 9/2014 |
| WO | 2019140240 A1 | 7/2019 |

OTHER PUBLICATIONS

European Search Report for EP21155336.7 issued Jul. 15, 2021; 4 pages.

* cited by examiner

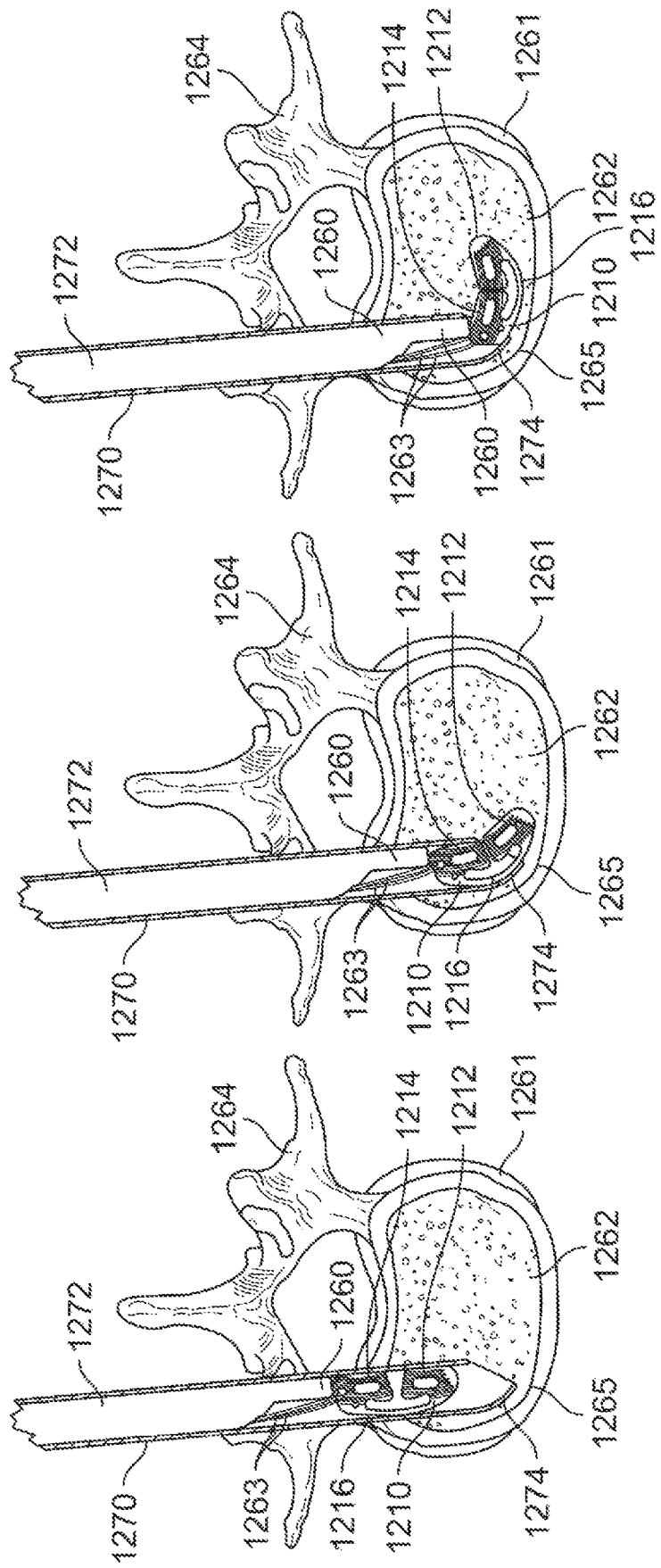

FLEXIBLE INTERBODY IMPLANT

BACKGROUND

This application is a continuation of U.S. application Ser. No. 17/162,357, filed on Jan. 29, 2021, which claims the benefit of the filing date of U.S. Provisional Patent Application No. 62/970,258 filed Feb. 5, 2020, the disclosures of which are hereby incorporated herein by reference.

BACKGROUND

Intervertebral implants are commonly used in spinal surgery, such as in interbody fusion procedures, in which an implant (e.g., a spacer or cage) is placed in the disc space between two vertebrae to be fused together. At least a portion of the disc is typically removed before the implant is positioned in the intervertebral space, and the implant may be supplemented with bone graft material to promote fusion of the vertebrae. Interbody fusion procedures may also be performed in conjunction with other types of fixation, such as pedicle screw fixation, to provide additional stability, particularly while the vertebrae fuse together.

Different interbody fusion procedures can be distinguished by their location along the spine (e.g., in the cervical, thoracic, or lumbar regions); by the type of implant used; and by the surgical approach to the intervertebral space, in which different surgical approaches often imply different structural characteristics of the implant or implants used. Different surgical approaches to the spine include anterior, posterior, and lateral. Examples of interbody fusion techniques performed along a posterior approach include posterior lumbar interbody fusion (PLIF) and transforaminal lumbar interbody fusion (TLIF). PLIF techniques typically include positioning two intervertebral implants into the intervertebral space along a posterior to anterior direction, with one implant being positioned towards the left side of the spine and one implant being positioned towards the right side of the spine. The implants used in such PLIF techniques typically have a straight shape, in that they extend along a central axis. TLIF techniques, by contrast, typically include positioning one intervertebral implant into the intervertebral space (often towards the anterior portion of the intervertebral space) from the posterior of the patient, but the spine is approached on one side from a more lateral position than in PLIF techniques. The implants used in such TLIF techniques are often curved, such that they have an overall kidney bean-like shape. Interbody fusion techniques performed along a lateral approach, on the other hand, often involve implants that are generally symmetric along their linear longitudinal axis (e.g., having a substantially rectangular or oval shape), but the implants are typically larger than those used in PLIF or TLIF techniques. That is, intervertebral implants used in lateral approaches often cover a substantial portion of the disc space.

Included among the different types of intervertebral implants are dynamic implants which, unlike static ones, have outer geometries that can be modified after the implant is inserted into the patient's body, such as within the intervertebral space. Examples of such dynamic intervertebral implants include those which can then be expanded in the superior-inferior direction, like those disclosed in U.S. Pat. No. 8,992,620 ("the '620 Patent") and in U.S. Patent Application Publication No. 2017/0290671 (hereinafter "the '671 Publication"), the disclosures of which are hereby incorporated by reference herein as if fully set forth herein. Such implants have an initially contracted configuration, so that they have a low profile in the superior-inferior direction to ease insertion into the intervertebral space, and then the implants are expandable after implantation so as to securely engage and stabilize the vertebrae on both sides of the intervertebral space. Other examples of dynamic implants are those which have a profile along the transverse plane that can be modified after insertion, such as the implant disclosed in U.S. Pat. No. 8,828,082 ("the '082 Patent"), the disclosure of which is hereby incorporated by reference herein as if fully set forth herein. That implant has portions which can be re-oriented with respect to one another in the transverse plane (i.e., within the plane of the intervertebral disc space), such that the implant has a generally linear profile along the insertion axis during movement into the disc space, after which the portions can be reoriented to provide stability over a larger area of the disc space (e.g., by changing to the curved, kidney bean-like shape of a typical TLIF implant). In that manner, the implant may allow for a less invasive approach by minimizing the cross-sectional area of the implant during insertion, without sacrificing the footprint taken up by the implant once implanted.

Although considerable effort has been devoted in the art to optimization of such intervertebral systems and methods, still further improvement would be desirable.

BRIEF SUMMARY

The present disclosure relates to an implant or cage that may have flexible portions enabling reversible elastic transition between a linear profile and a curved or kidney bean-like shape on a plane corresponding to a transverse plane of a patient relative to an intended final position of the cage. The cage may include two body portions or wings connected by a bridge. The wings may have a round or oblong cross-section on the transverse plane and may be thicker on the transverse plane than the bridge. The relatively thin cross-section of the bridge on the transverse plane may enable flexure of the bridge corresponding to movement and reorientation of the wings relative to each other. The elastic flexibility of the bridge may be facilitated by a pattern of apertures perforating the bridge. A variety of patterns of apertures may contribute to the elastic flexibility of the bridge.

In another aspect, a lumbar interbody fusion device may include a first wing, a second wing, and a bridge. The bridge may have an arcuate resting shape and include a first end connected to the first wing, a second end connected to the second wing, and at least one aperture extending through the bridge in a radial direction relative to the arcuate resting shape of the bridge. The bridge may be elastically deformable such that a distance between the first wing and the second wing may vary according to elastic deformation of the bridge.

In some arrangements according to any of the foregoing, a method of constructing the device may include additively manufacturing the device by stacking layers in an axial direction perpendicular to the radial direction.

In some arrangements according to any of the foregoing, the layers may be layers of titanium.

In some arrangements according to any of the foregoing, the first wing may have a V shaped recess that is concave toward the second wing and the second wing may have a V shaped projection that is convex toward the first wing, and the V shaped projection may extend into the V shaped recess when the bridge is in the resting shape.

In some arrangements according to any of the foregoing, the arcuate resting shape of the bridge may be centered on an axis extending perpendicular to the radial direction and extending from an inferior direction to a superior direction, and the wings are radially inward of the bridge.

In some arrangements according to any of the foregoing, the at least one aperture may be a plurality of slots extending across bridge from an inferior edge of the bridge and from a superior edge of the bridge to define a serpentine bar shape of the bridge.

In some arrangements according to any of the foregoing, a cavity may extend through the bridge between the first and the second end. The at least one aperture may include a spiral slot extending along the bridge between the first end and the second end. The spiral slot may provide an opening from the cavity to an exterior surface of the bridge.

In some arrangements according to any of the foregoing, the bridge may be a coil shaped element extending from the first end to the second end.

In some arrangements according to any of the foregoing, the axis may be perpendicular to a flexure plane. A width of the bridge may be defined parallel to the axis, and the width of the bridge may be greater than a radial thickness of the bridge on the flexure plane at every location between the first end and the second end.

In some arrangements according to any of the foregoing, flexure of the bridge perpendicular to its width may correspond to movement of the first wing and second wing along the flexure plane.

In another aspect according to any of the foregoing, a method of assembling an interbody device may include positioning a first wing adjacent a second wing such that a fulcrum extending from the first wing extends along a fulcrum axis toward a socket included by the second wing, inserting the fulcrum into the socket, and rotating the first wing relative to the second wing such that the fulcrum turns within the socket about the fulcrum axis.

In some arrangements according to any of the foregoing, the fulcrum engages tabs partially enclosing the socket, thereby preventing withdrawal of the fulcrum from the socket along the fulcrum axis when the rotating step is completed.

In some arrangements according to any of the foregoing, the rotating step is completed when a first channel extends through the first wing is aligned with a second channel extending through the second wing.

In some arrangements according to any of the foregoing, the method includes a step of inserting a leaf spring through the aligned first channel and second channel.

In another aspect according to any of the foregoing, a lumbar interbody fusion device may comprise a first wing, a second wing, and an elastic biasing element maintaining the first wing and the second wing in contact with one another at a pivoting contact point. The first wing and the second wing may be freely separable from one another absent the biasing element.

In some arrangements according to any of the foregoing, the elastic biasing element may include a first end bearing on the first wing and a second end bearing on the second wing and being oriented to bias the first wing relative to the second wing about the pivoting contact point toward a rest position.

In some arrangements according to any of the foregoing, the biasing element may be a coil spring.

In some arrangements according to any of the foregoing, the biasing element may be a leaf spring.

In some arrangements according to any of the foregoing, the first wing may include a first outer facet and a first inner facet and may be movable about the pivoting contact point between a first position in which the first outer facet bears on the second wing and a second position in which the first inner facet bears on the second wing.

In some arrangements according to any of the foregoing, the first wing may define a vertex between the first inner facet and the first outer facet upon which the first wing rocks when rotating about the pivoting contact point.

BRIEF DESCRIPTION OF THE DRAWINGS

FIGS. 12A-12C are section views taken along a transverse plane of a patient with a cage according to any of the above arrangements in progressive degrees of deployment.

DETAILED DESCRIPTION

When referring to specific directions and planes in the following disclosure, it should be understood that, as used herein, the term "proximal" means closer to the operator/surgeon, and the term "distal" means further away from the operator/surgeon. The term "anterior" means toward the front of the body or the face, and the term "posterior" means toward the back of the body. With respect to the longitudinal axis of the spine, the term "superior" refers to the direction towards the head, and the term "inferior" refers to the direction towards the pelvis and feet. The "transverse plane" is that plane which is orthogonal to the longitudinal axis of the spine. The "coronal plane" is a plane that runs from side to side of the body along the longitudinal axis of the spine and divides the body into anterior and posterior portions. The "sagittal plane" is a plane that runs along the longitudinal axis of the spine and defines a plane of symmetry that separates the left and right sides of the body from each other. Finally, the "medial" refers to a position or orientation toward the sagittal plane, and lateral refers to a position or orientation relatively further from the sagittal plane.

Figure 1A:
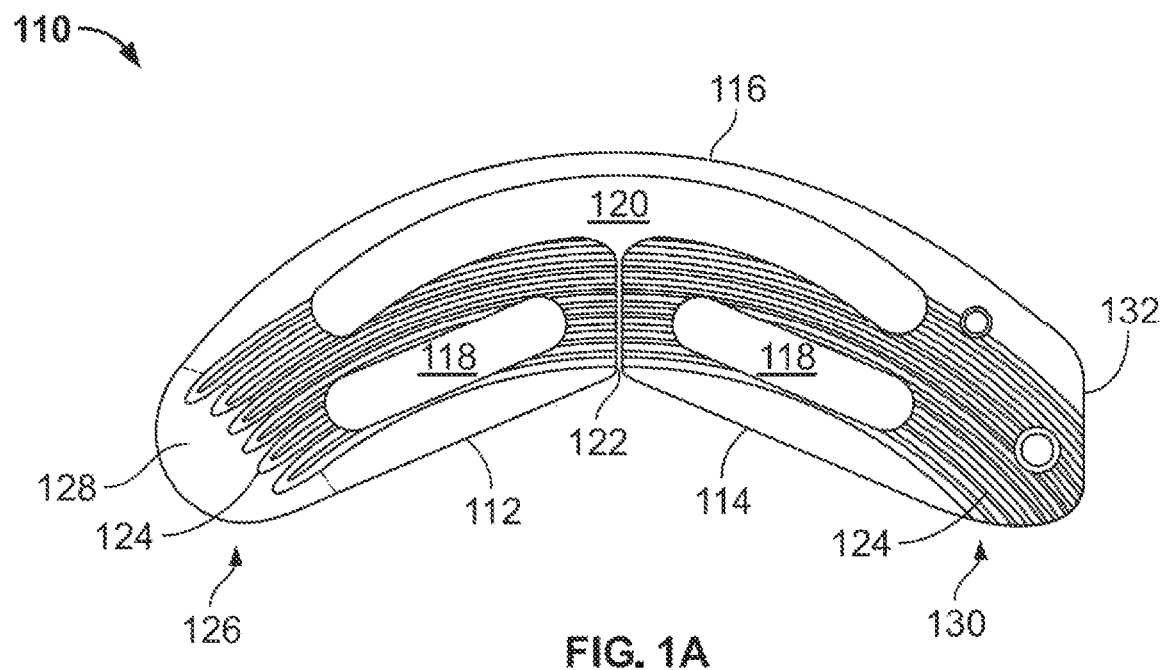
FIGS. 1A and 1B are top plan and side elevation views, respectively, illustrating a cage according to a first arrangement.
Figure 1B:
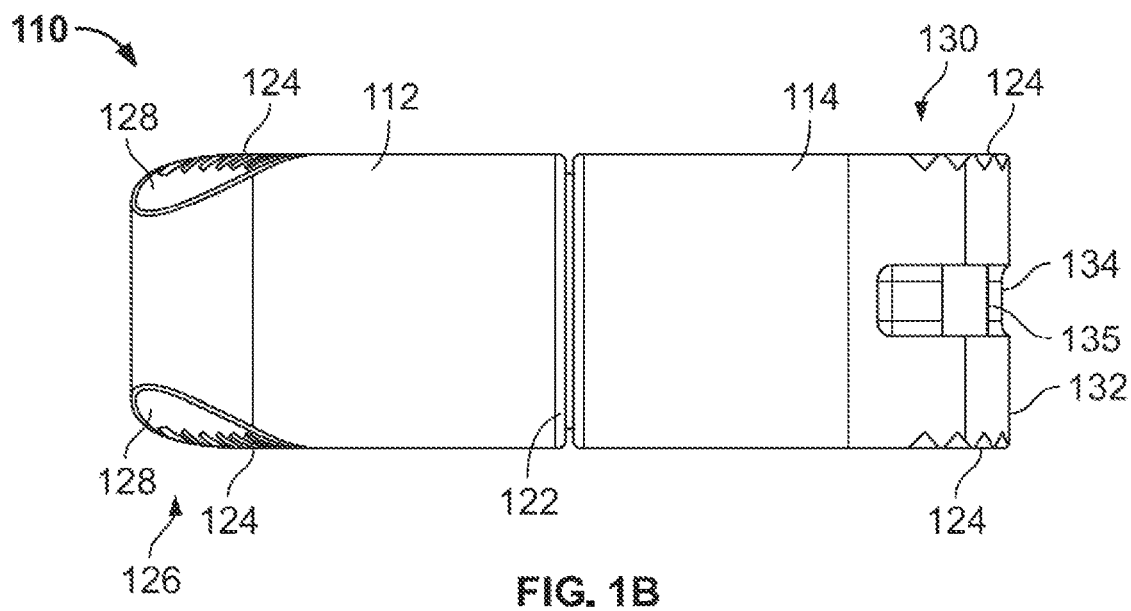

FIGS. 1A and 1B illustrate a cage 110 according to an embodiment of the present disclosure. Cage 110 includes a distal wing 112 and a proximal wing 114 joined to each other by a flexible bridge 116. Bridge 116 defines an arcuate shape having a generally constant radius relative to an axis (not pictured) along a length of bridge 116, which axis extends generally in the superior-inferior direction in the implanted state of the cage 110. The terms radial, axial, circumferential, and tangential as used throughout this disclosure will indicate directions relative to that superior-inferior axis about which the arc of bridge 116 extends.

Both wings 112, 114 have similar roughly ovoid axial cross-sections. A radial gap 120 exists between wings 112, 114 and bridge 116, and wings 116 are separated by seam 122. Radial gap 120 cooperates with the flexibility of bridge 116 such that bridge 116 acts as a living hinge and enables variation in a width of seam 122 and the radius of bridge 116. Bridge 116 may be formed of any elastically flexible biocompatible material, meaning bridge 116 is internally biased toward a neutral radius or position. Example materials for the bridge 116 and the cage 110 as a whole include biocompatible polymers (e.g., polyether ether ketone (PEEK)), elastomeric materials, shape memory polymers, and shape memory metals (e.g., nitinol). In some arrangements, the neutral radius of bridge 116 results in a narrow seam 122 as shown in FIGS. 1A and 1B. In other arrangements, the neutral radius of bridge 116 is smaller than shown in FIGS. 1A and 1B, so bridge's 116 internal bias presses wings 112, 114 into abutment.

Wings 112, 114 include axial through holes 118. Through holes 118 are illustrated as oblong in shape, but in other arrangements may be in other shapes. Such through holes 118 contribute to bone in-growth after cage 110 is implanted, and the though holes may be packed with bone growth promoting material (e.g., autologous and/or allogeneic bone graft, a bone growth enabling matrix, and/or bone growth stimulating substances). Axial surfaces of wings 112, 114 include ridges 124 which prevent slippage of cage 110 and may further facilitate in-growth.

Bridge 116 meets distal wing 112 near a distal end 126 of cage 110 and meets proximal wing 114 near a proximal end 130 of cage 110. Distal end 126 of cage 110 includes bevels 128 between a distal circumferential surface and the axial surfaces of cage 110. Proximal end 130 includes a flat proximal surface 132 extending perpendicular to a longest dimension of cage 110. An attachment structure may be provided at the proximal end 130 of the cage 110 for connection to a portion of a delivery tool (not shown) for inserting and positioning the cage 110 within the intervertebral space. The attachment structure may include a notch 134 cut into cage 110 at proximal end 130 and extending partially across flat proximal surface 132. A pin 135 extending generally parallel to the axial direction may be positioned within the notch 134. That pin 135 may be configured to be grasped by a portion of the delivery tool such that the cage 110 can be pivoted about the longitudinal axis of pin 135. A suture may also be looped around pin 135 before delivery of cage 110. The notch 135 and pin 135 together provide a hitch for the suture.

Elastic flexibility and durability of designs of bridge 116 consisting of a single, continuous strip of material may be limited, particularly where the implant is made of a relatively stiff or rigid material such as titanium. For example, such bridge designs may only flex only across a relatively small range or only a relatively small number of times before bridge 116 deforms permanently or fractures. Variations of bridge's 116 design may enable bridge 116 to elastically deform across a greater range or a greater number of times, which can be beneficial to various methods for delivering bridge. In one example, bridge 116 may be modified to include a number of apertures or openings extending radially therethrough. Certain such perforated designs of bridge 116 may have greater elastic flexibility than a solid bridge 116 of the same material.

Figure 2A:
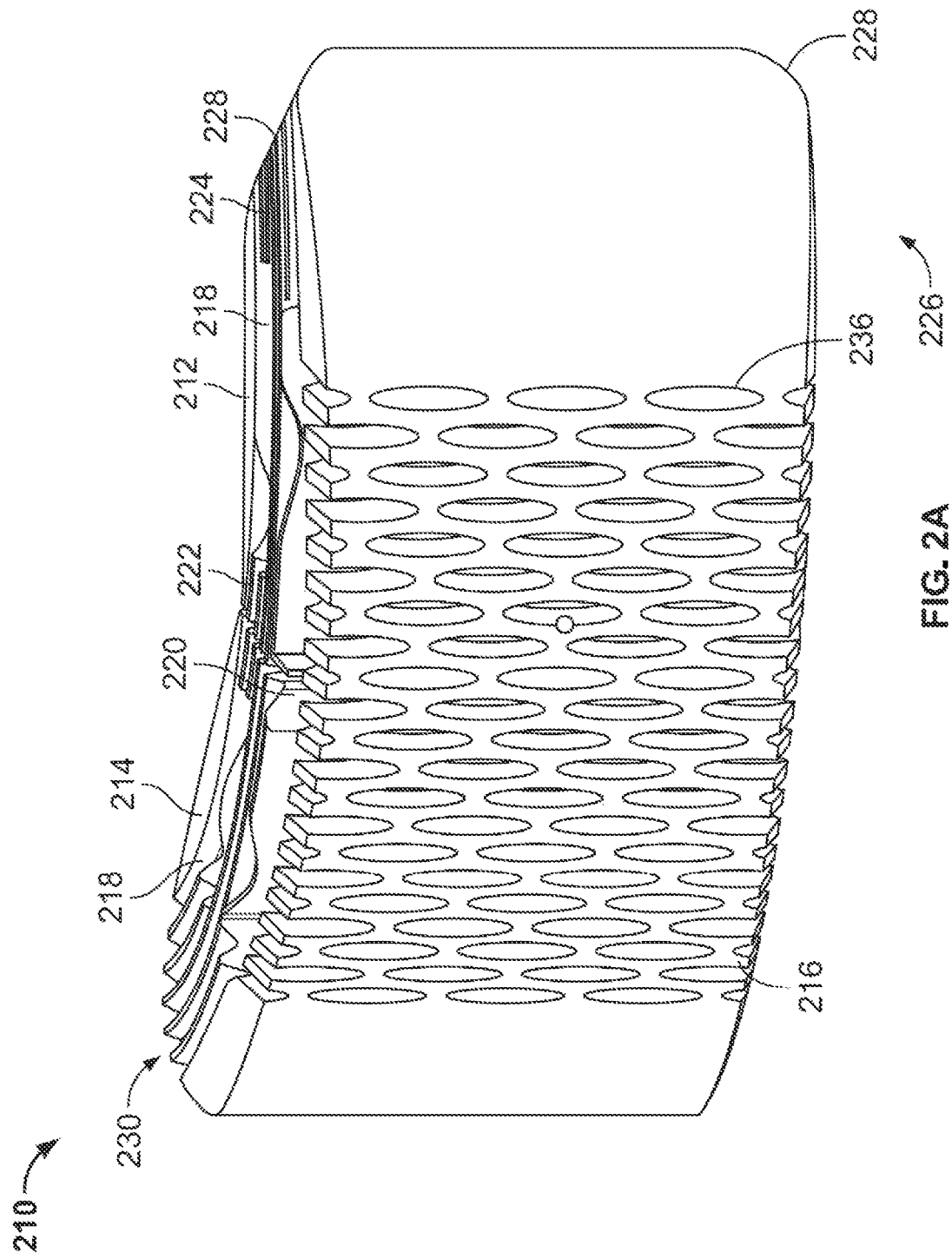
FIGS. 2A-2B are oblique perspective views illustrating a cage according to a second arrangement.
Figure 2B:
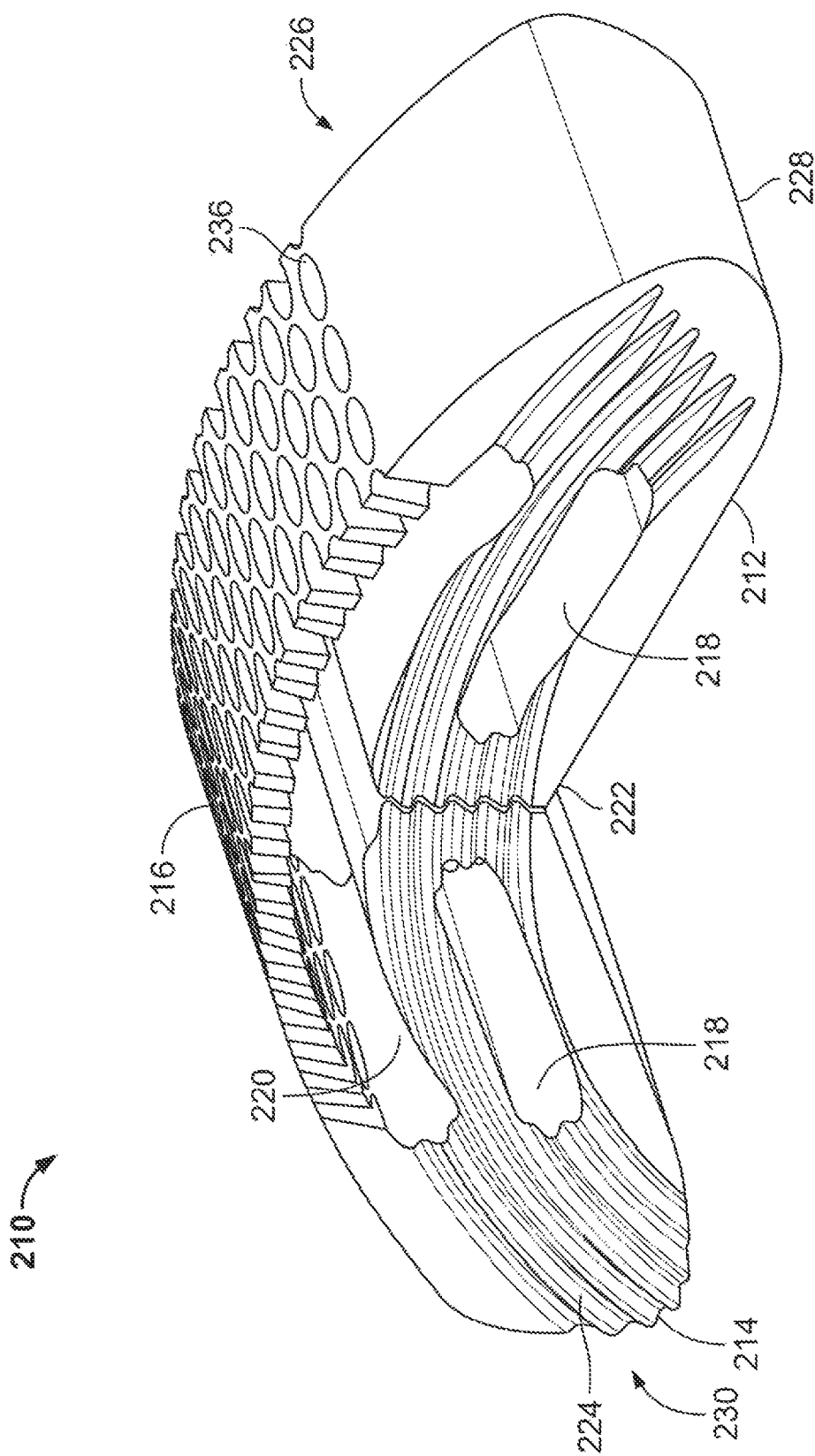

FIGS. 2A and 2B illustrate a cage 210 according to another arrangement. Cage 210 shares features in common with cage 110, and like numerals indicate like elements except where stated otherwise. For example, cage 210 includes distal wing 212 and proximal wing 214 similar to distal wing 112 and proximal wing 114, and through holes 218 and a radial gap 220 similar to through holes 118 and radial gap 118, respectively, of cage 110. Bridge 216 of cage 210 includes perforations 236 extending radially through bridge 216. As illustrated, perforations 236 each have an oval shape with a longest dimension extending axially along bridge 216. Perforations 236 are arranged in a staggered pattern of axially extending columns such that each whole perforation 236 (as opposed to partial length perforations 236 terminating on axial edges of bridge 216) is axially centered on a space between two mutually axially adjacent perforations 236 in any radially adjacent columns Perforations 236 alter flexibility characteristics of bridge 216. Bridge 216 having perforations 236 as illustrated may be able to bend more easily or further without fracture than an unperforated bridge 216 constructed of the same material.

Cage 210, or any other cage described in the present disclosure, may be additively manufactured. Examples of additive manufacturing processes for creating some or all of the components of cage 210, or other cages disclosed herein, are disclosed in U.S. Pat. Nos. 7,537,664, 8,147,861, 8,350,186, 8,728,387, 8,992,703, 9,135,374, 9,180,010, and 9,456,901 as well as U.S. Patent Application Publication No. 2006/0147332, all of which are hereby incorporated by reference.

Figure 3:
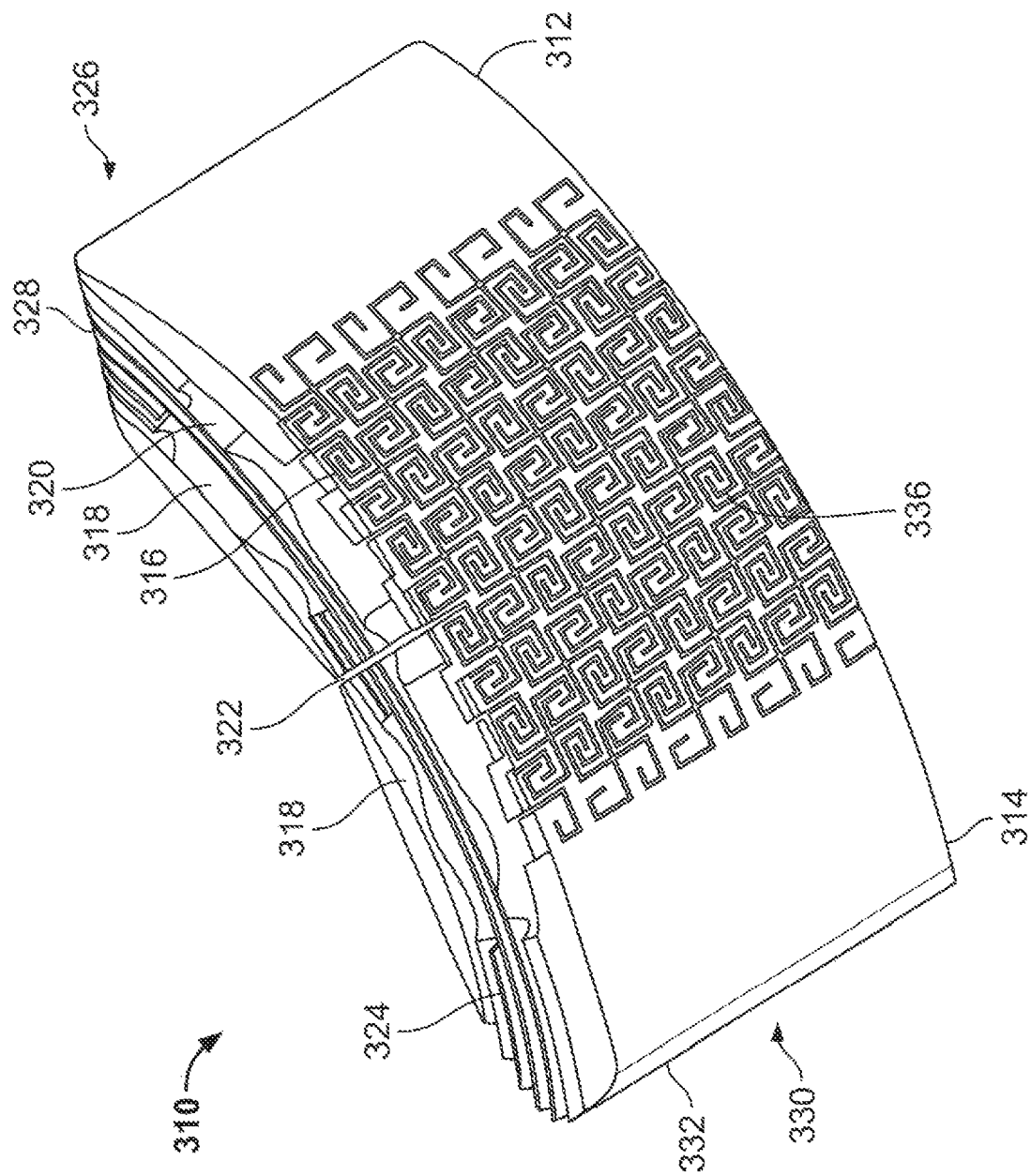
FIG. 3 is an oblique perspective view illustrating a cage according to a third arrangement.

FIG. 3 shows a cage 310 having a bridge 316 that includes a pattern of interlocking right-angle hooks 336. The pattern of interlocking hooks 336 facilitates reversible flexure of bridge 316 similarly to perforations 236. The hooks 336 are provided by cuts extending radially through bridge 316. The hooks 336 each include a series of linear components with right angle bends between the components. The hooks 336 branch outward from cross-points, and the right angle bends in each hook 336 are clockwise as the hook extends away from the respective cross-point. In other arrangements, however, hooks 336 may be provided by lines extending in directions having both circumferential and axial components.

The pattern of interlocking hooks 336 particularly facilitates localized flexibility of bridge 316. For example, hooks 336 enable bridge 316 to deform at and around a contact point of an applied load while areas of bridge 316 further from the contact point exhibit little or no deformation from a rest position in response to the applied load.

Figure 4:
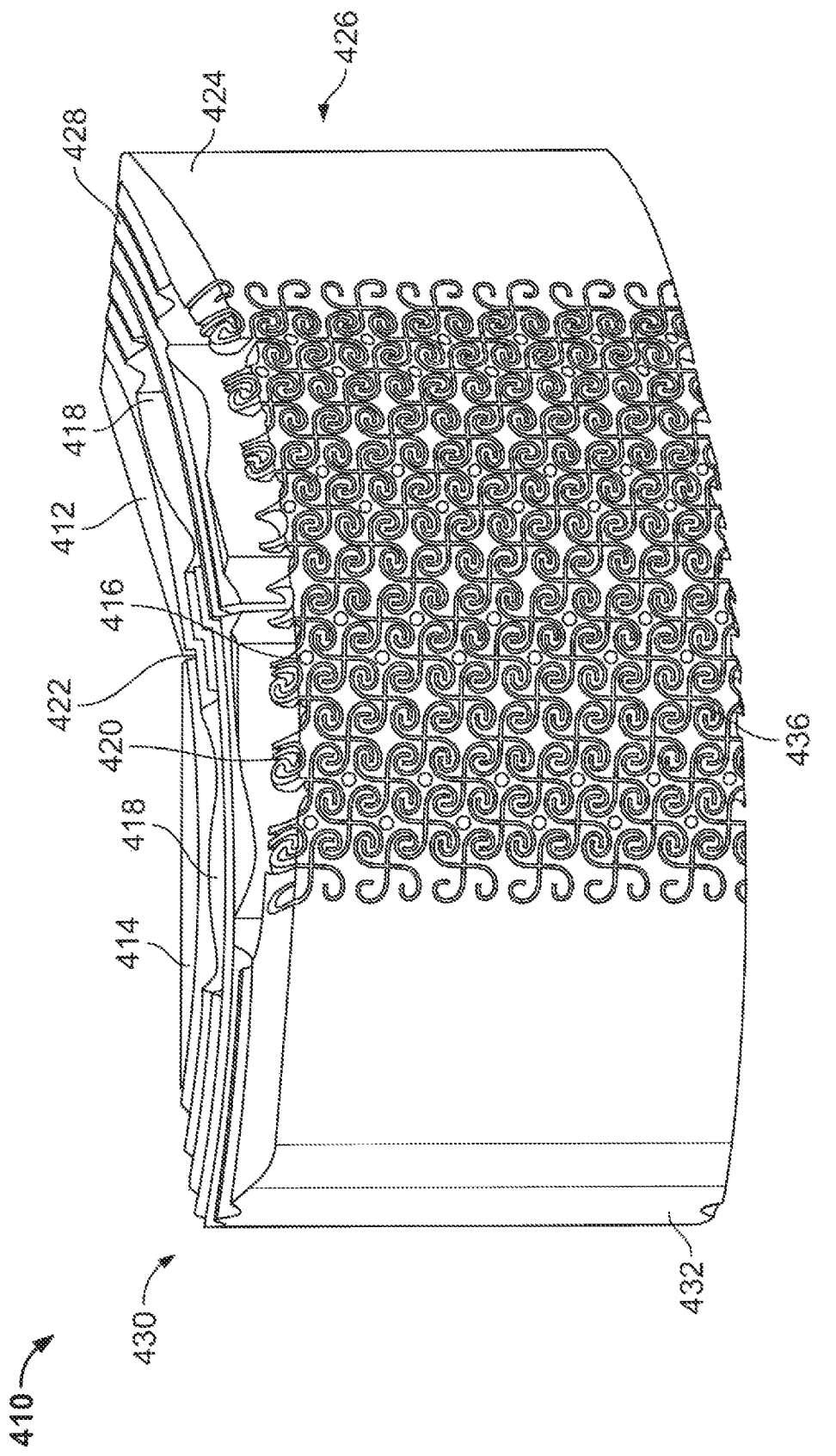
FIG. 4 is an oblique perspective view illustrating a cage according to a fourth arrangement.

FIG. 4 shows an arrangement of cage 410 with hooks 436 similar to hooks 336 illustrated in FIG. 3. However, hooks 436 are provided by branching curved lines intersecting at approximately right angles. Hooks 436 similarly contribute to flexure of bridge 416.

Figure 5:
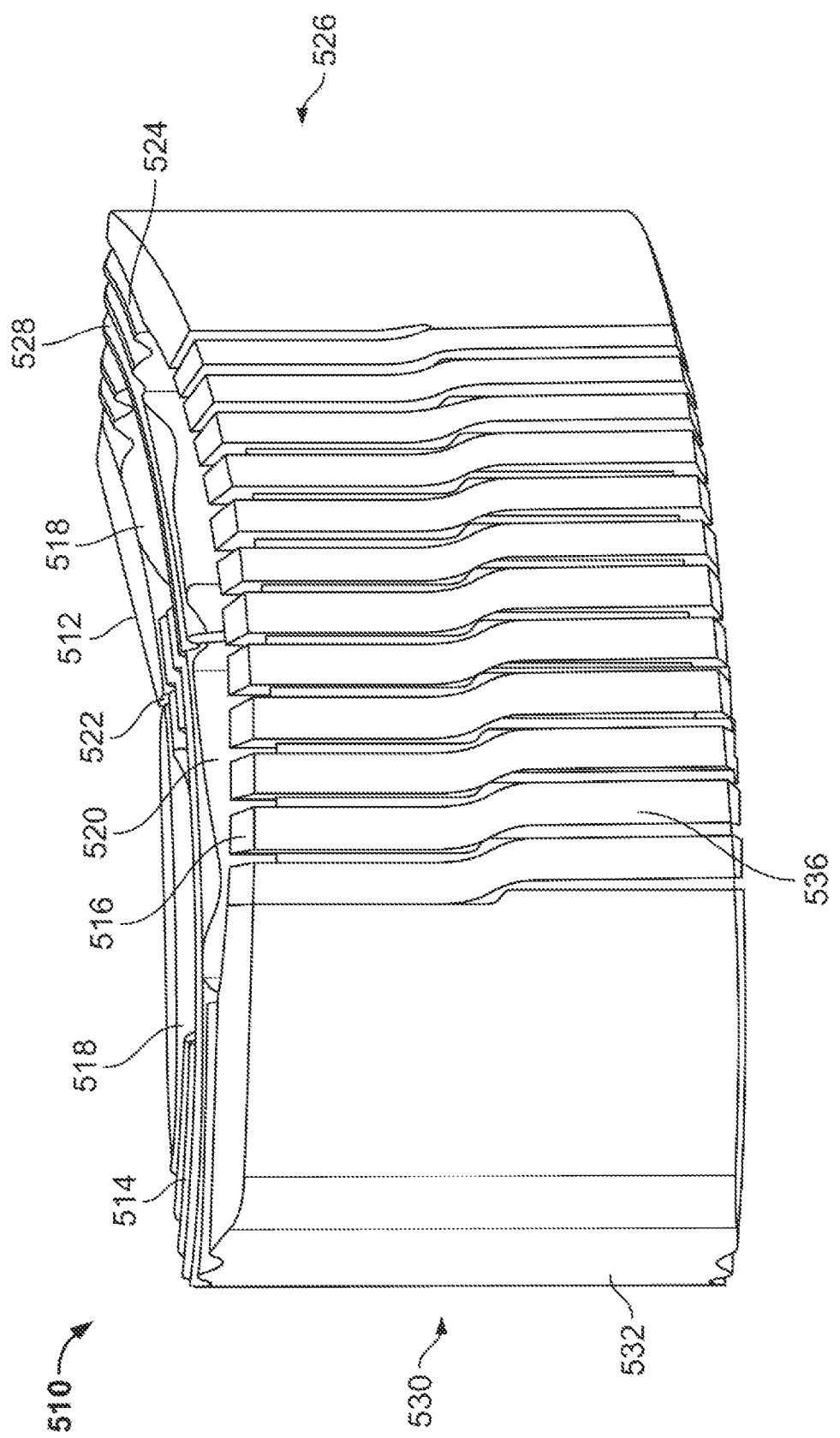
FIG. 5 is an oblique perspective view illustrating a cage according to a fifth arrangement.

In the arrangement illustrated in FIG. 5, bridge 516 is a helical coil extending circumferentially from distal wing 512 to proximal wing 514. The helical coil shape is provided by helical void 536 bounding bridge 516.

Figure 6:
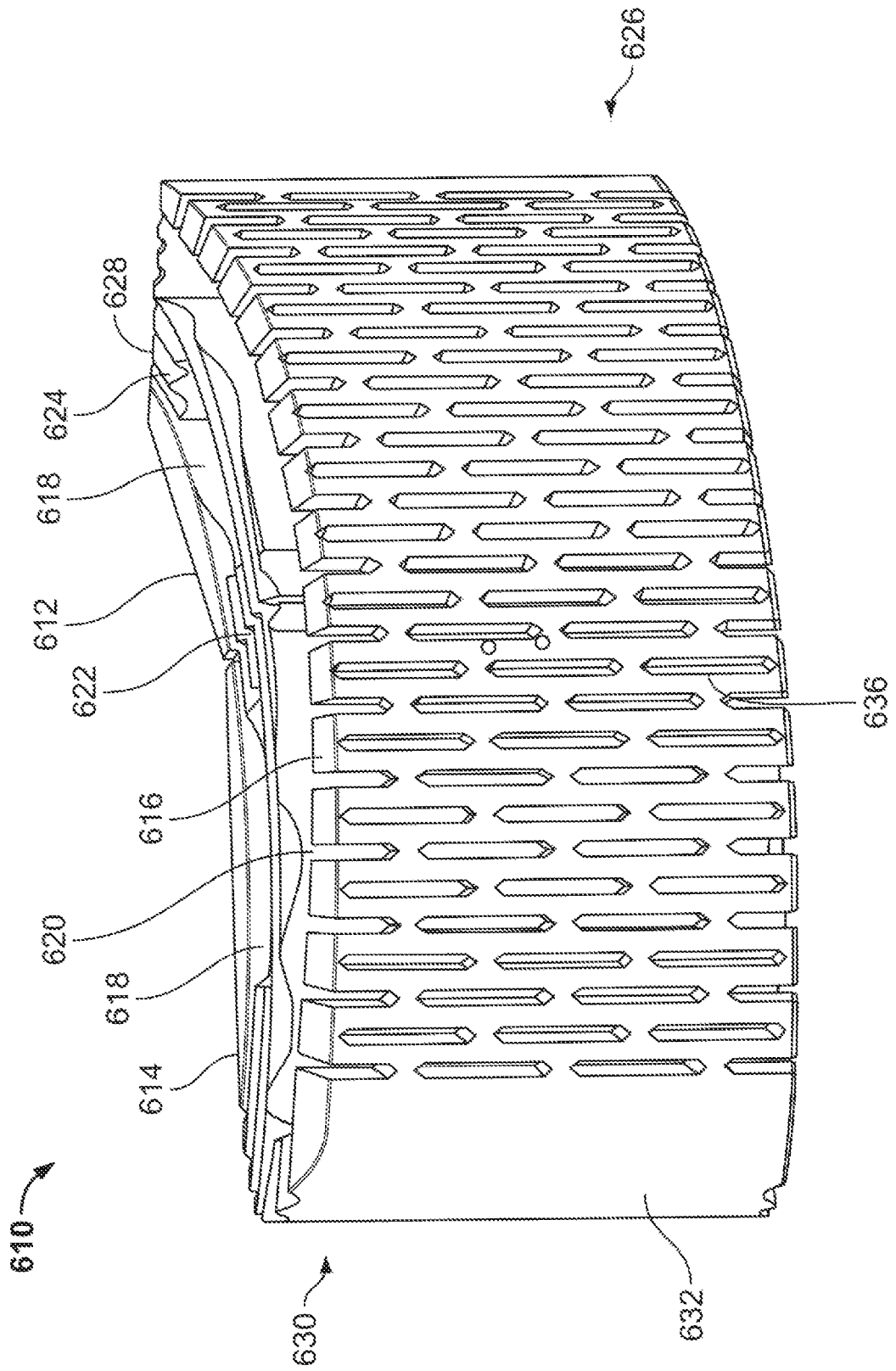
FIG. 6 is an oblique perspective view illustrating a cage according to a sixth arrangement.

In the arrangement illustrated in FIG. 6, bridge 616 includes several axial columns of shorter slots 636 extending axially across bridge 616. Circumferentially adjacent columns of slots 636 are axially staggered relative to each other such that each whole slot 636 (as opposed to partial slots 636 terminating at axial edges of bridge 616) is axially centered on a space between two mutually axially adjacent slots 636 in any radially adjacent columns Bridge 616 is also longer relative to wings 612, 614 and attaches to wings 612, 614 further from seam 622 than the bridges shown above in FIGS. 1-5, further contributing to flexibility of cage 610. However, it should be understood that the bridge length and attachments shown in FIG. 6 may be used in any of the other arrangements throughout the present disclosure, and the slots 636 may be applied to a bridge having the length and attachment locations shown in any of the other arrangements throughout the present disclosure.

Figure 7:
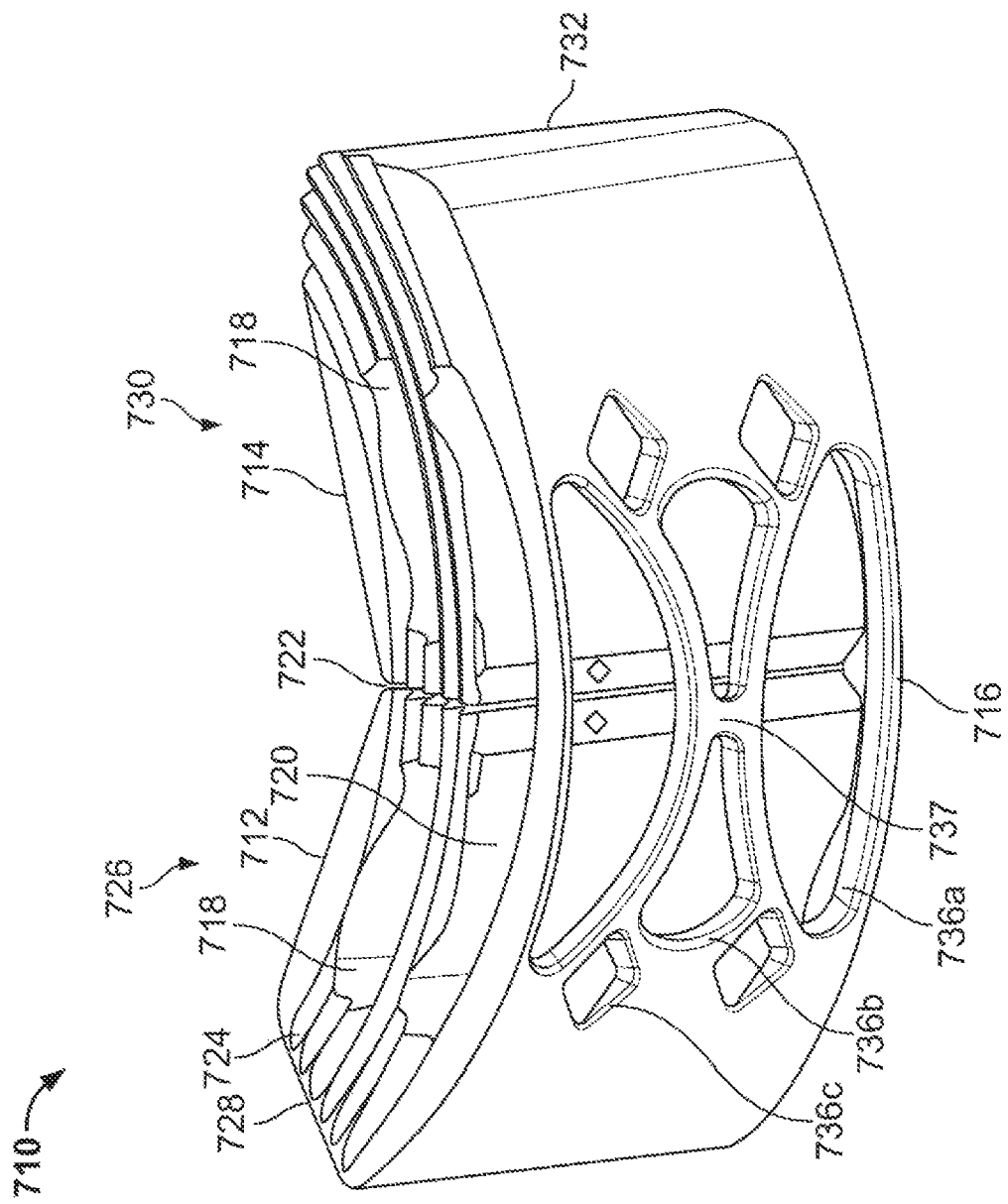
FIG. 7 is an oblique perspective view illustrating a cage according to a seventh arrangement.

FIG. 7 illustrates an arrangement of cage 710 with multiple differently-shaped through holes 736a, 736b, 736c extending radially through bridge 716. Opposed arches 736a extend circumferentially parallel to axial edges of bridge 716 and curve axially toward each other. Arches nearly meet at an axial midpoint of bridge 716 that is circumferentially aligned with seam 722, and a bridging connection 737 may connect the apexes of the arches 736a together. Wedges 736b fill much of two axial spaces between either circumferential sides of arches 736a, but each wedge 736 tapers inward to a point at its end closest to the seam 722. Diamonds 736c fill four axial spaces between wedges 736b and arches 736a, but extend circumferentially beyond wedges 736b and arches 736a such that circumferential midpoints of diamonds 736c are approximately circumferentially aligned with ends of wedges 736b and arches 736a. The above described design of through holes 736a, 736b, 736c provides bridge 716 with flexibility and a relatively simple design. The relative simplicity of bridge 716 can result in a shorter production time for cage 710 depending on the chosen method of manufacture.

Figure 8A:
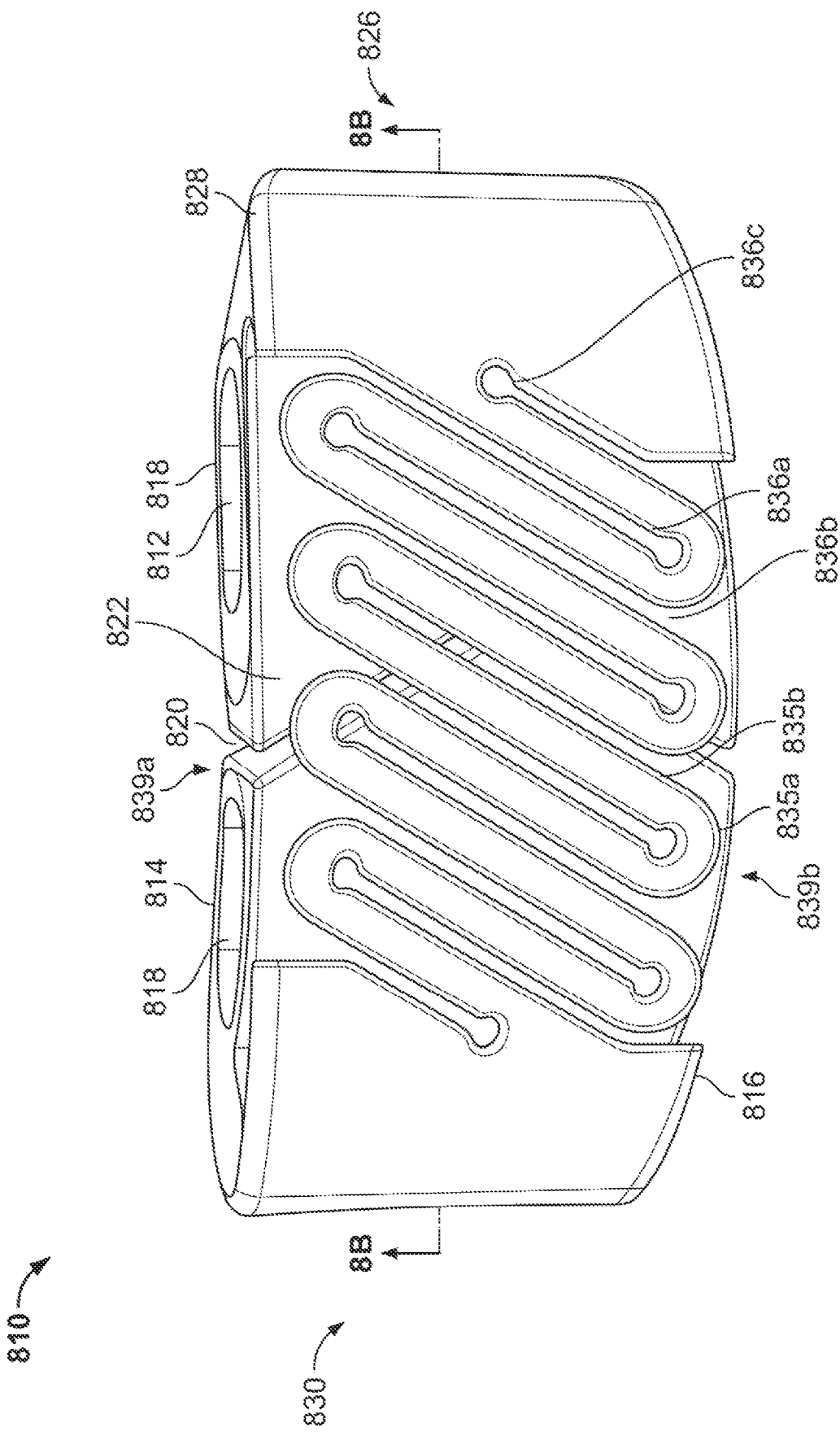
FIG. 8A is an oblique perspective view illustrating a cage according to an eighth arrangement.
Figure 8B:
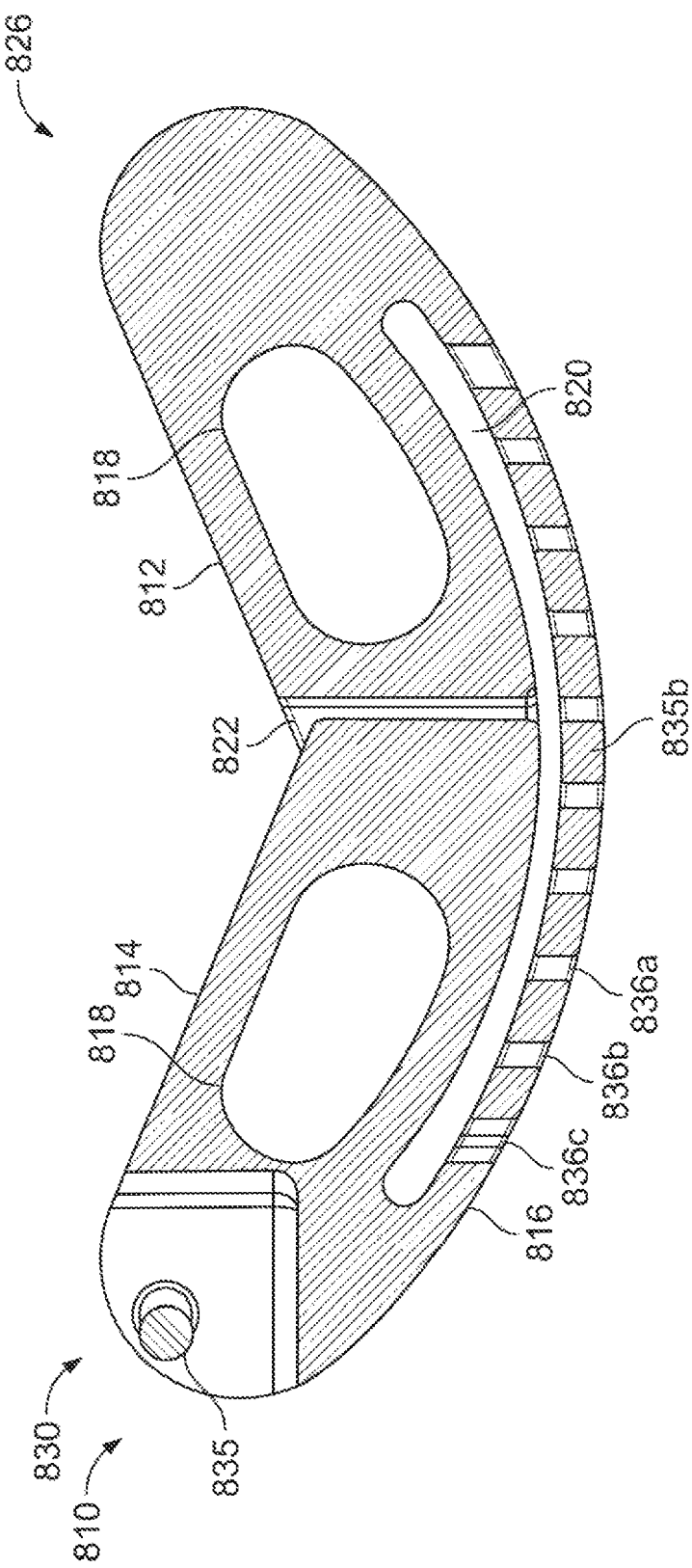
FIG. 8B is a section view taken along line 8B-8B of FIG. 8A.

Bridge 816 of the arrangement shown in FIGS. 8A and 8B includes a serpentine bar 835 defined between two rows of slots 836, namely a superior row 836a and an inferior row 836b. The slots in the superior row 836a extend from the superior end 839a of the bridge towards the inferior end 839b but stop short of the inferior end 839b, and the slots in the inferior row 836b likewise extend from the inferior end 839b of the bridge towards the superior end 839a but stop short of the superior end 839a. In that manner, the slots 836a, 836b define curved sections 835a of the bar 835 connecting adjacent straight sections 835b of the bar, where successive curved sections 835a alternate between being positioned at the superior end 839a and the inferior end 839b of the bridge. The orientation of the superior and inferior directions relative to the distal end 826 and proximal end 830 described here is merely exemplary and may be reversed in other examples. Further, though the illustrated example shows the slots 836 extending proximally as they extend from the inferior end 839b to the superior end 839a, slots 836 according to other examples may extend proximally as they extend from the inferior end 839b to the proximal end 839a. The slots in both rows of slots 836a, 836b each extend along a direction that has both axial and circumferential components. For example, the slots 836a, 836b, and thus the intervening straight sections 835b of the bar 835, may extend generally along a coronal plane of the body while oriented at a 30° angle to the medial-lateral axis as illustrated. Though straight sections 835b of the illustrated arrangement extend at a 30° relative to the medial-lateral axis, other angles may be suitable. Angles from 30° to 60° are explicitly contemplated. The slot 836b in each row of slots 836b that is circumferentially terminal in the direction of the row's circumferential component is shorter than the other slots 836b. In the illustrated example, the shorter slots 836b extend to an axial midpoint of bridge 816. Each slot 836b ends in a circular node 836c having a greater diameter than a width of the slots 836b, further contributing to flexibility of bridge 816 and reducing stress concentration.

Figure 9A:
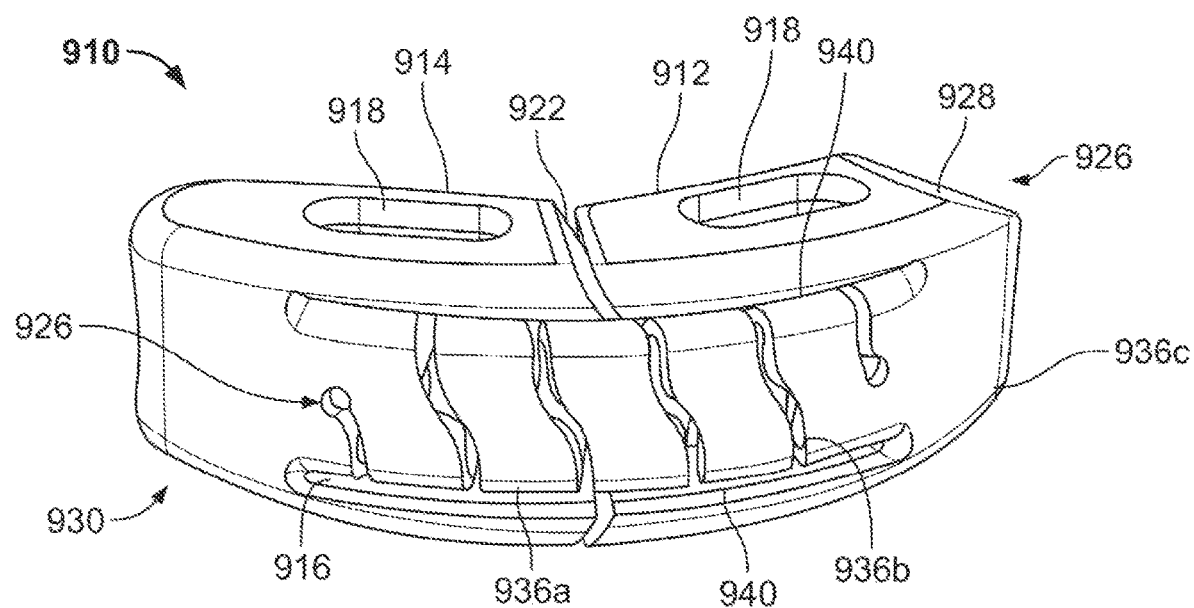
FIG. 9A is an oblique perspective view illustrating a cage according to a ninth arrangement.
Figure 9B:
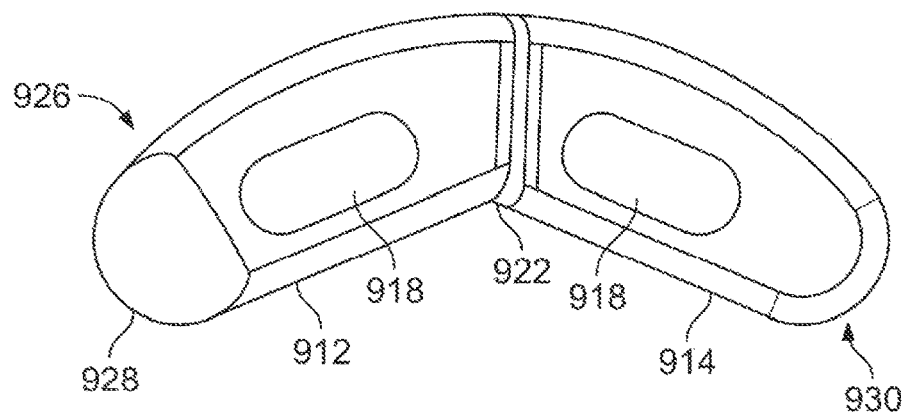
FIGS. 9B-9D are top plan, side elevation, and rear elevation views, respectively, illustrating the cage according to the ninth arrangement.
Figure 9D:
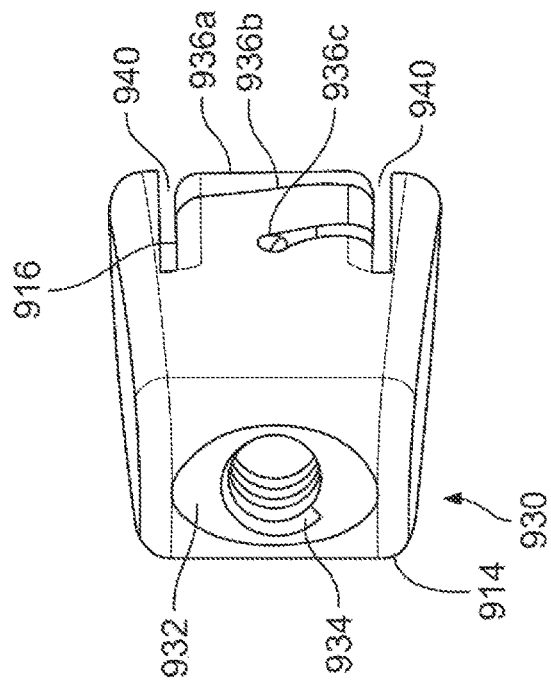
Figure 9C:
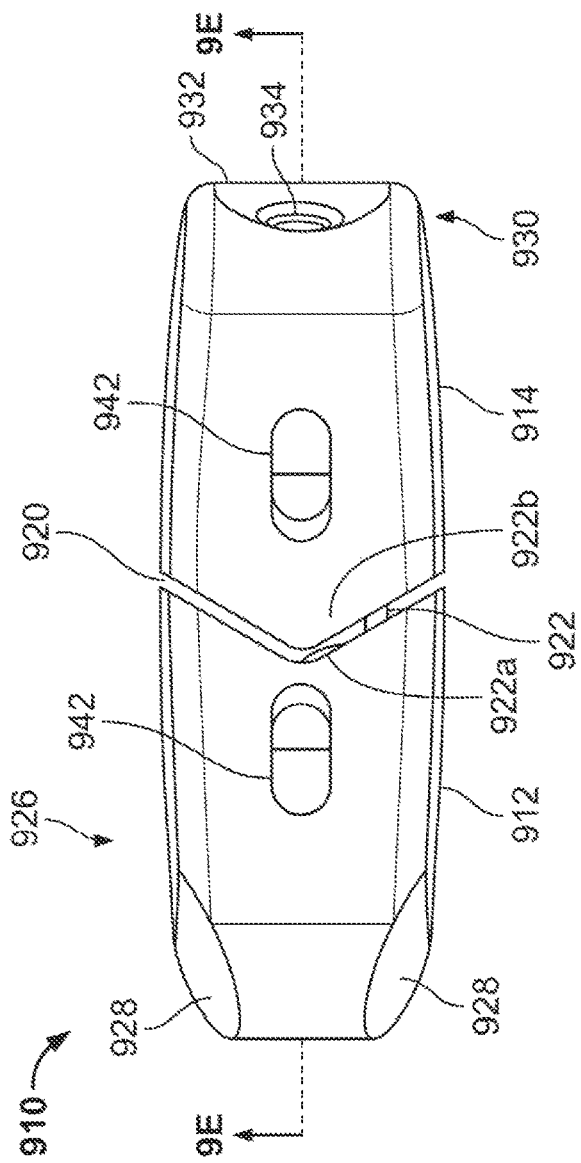
Figure 9E:
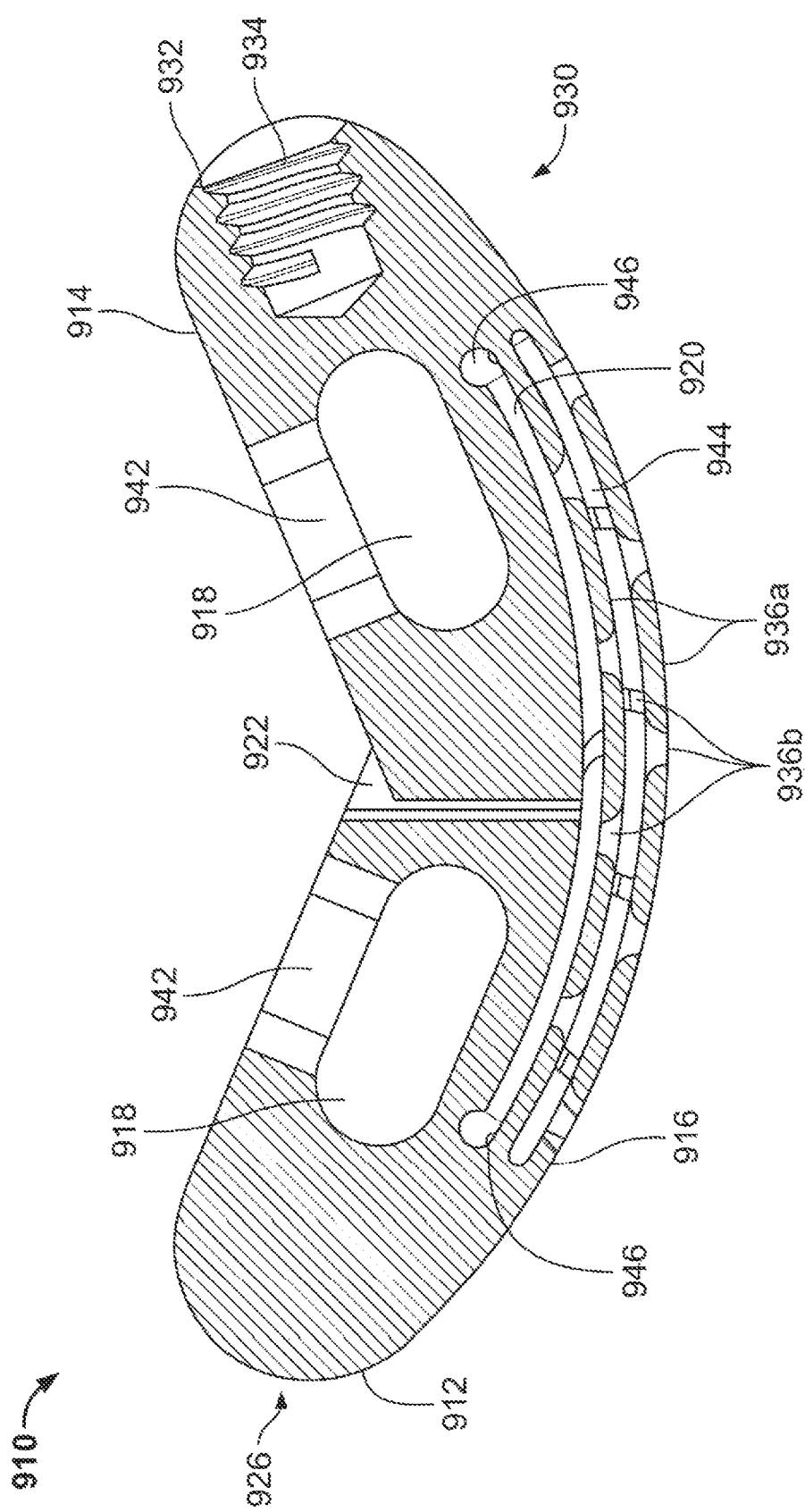
FIG. 9E is a section view taken along line 9E-9E of FIG. 9C.

FIGS. 9A-9E illustrate a cage 910 with a bridge 916 provided by a coil 936a, similar to that described above with regard to FIG. 5, with FIG. 9E being a sectional view along section line 9E of FIG. 9C, corresponding to an axial cross-section at an axial midpoint of cage 910. Coil 936a is partially defined by spiral slot 936b extending circumferentially along bridge 916. Both ends of slot 936b end in a circular node 936c on a radially outer surface of bridge 916. Nodes 936c each have a greater diameter than a width of slot 936b. Coil 936a surrounds a circumferentially extending cavity 944 within bridge 916. Axial surfaces of wings 912, 914 at both the superior end and the inferior end of the cage 910 extend radially over radial gap 920 and bridge 916, defining axial gaps 940 between overhanging portions of the superior and inferior surfaces and the bridge 916. Both circumferential ends of radial gap 920 end in an approximately cylindrical axial column 946 having a greater diameter than a radial thickness of radial gap 920.

Each wing 912, 914 includes a radial port 942 extending from a radially interior surface of the respective wing 912, 914 to a respective axial through hole 918. An attachment structure may be provided at the proximal end 930 of the cage 910 for connection to a portion of a delivery tool (not shown) for inserting and positioning the cage 910 within the intervertebral space. For example, proximal wing 914 may include a threaded bore 934 at proximal end 930, which threaded bore 934 may extend distally from a concavity 932 defined in the proximal end 930. Seam 922 has a chevron shape with its peak oriented in a distal direction toward distal wing 912. The chevron shape is provided by a "V" shaped recess 922a in distal wing 912 that is concave toward proximal wing 914 and a "V" shaped projection 922b on proximal wing 914 that is convex toward distal wing 912. When cage 910 is in a resting shape, the "V" shaped 922b projection extends into the "V" shaped recess 922a, thereby defining seam's 922 chevron shape. The chevron shape of seam 922 allows portions of the cage 910 to be self-supporting, which enables additive manufacturing of cage 910 without the need for (or with only minimal) sacrificial support structures. For example, the chevron shape simplifies printing of cage 910 in a vertical orientation, such as the orientation of cage 716 shown in FIG. 7. Further, the chevron seam 922 could be applied to other constructions of cage 910. For example, any of the other arrangements of cages described above or below in the present disclosure may be constructed with a chevron seam similar to seam 922 as illustrated in FIG. 9C. Furthermore, in any arrangement, the chevron seam may be constructed with its peak pointed in the proximal or distal direction.

Figure 10A:
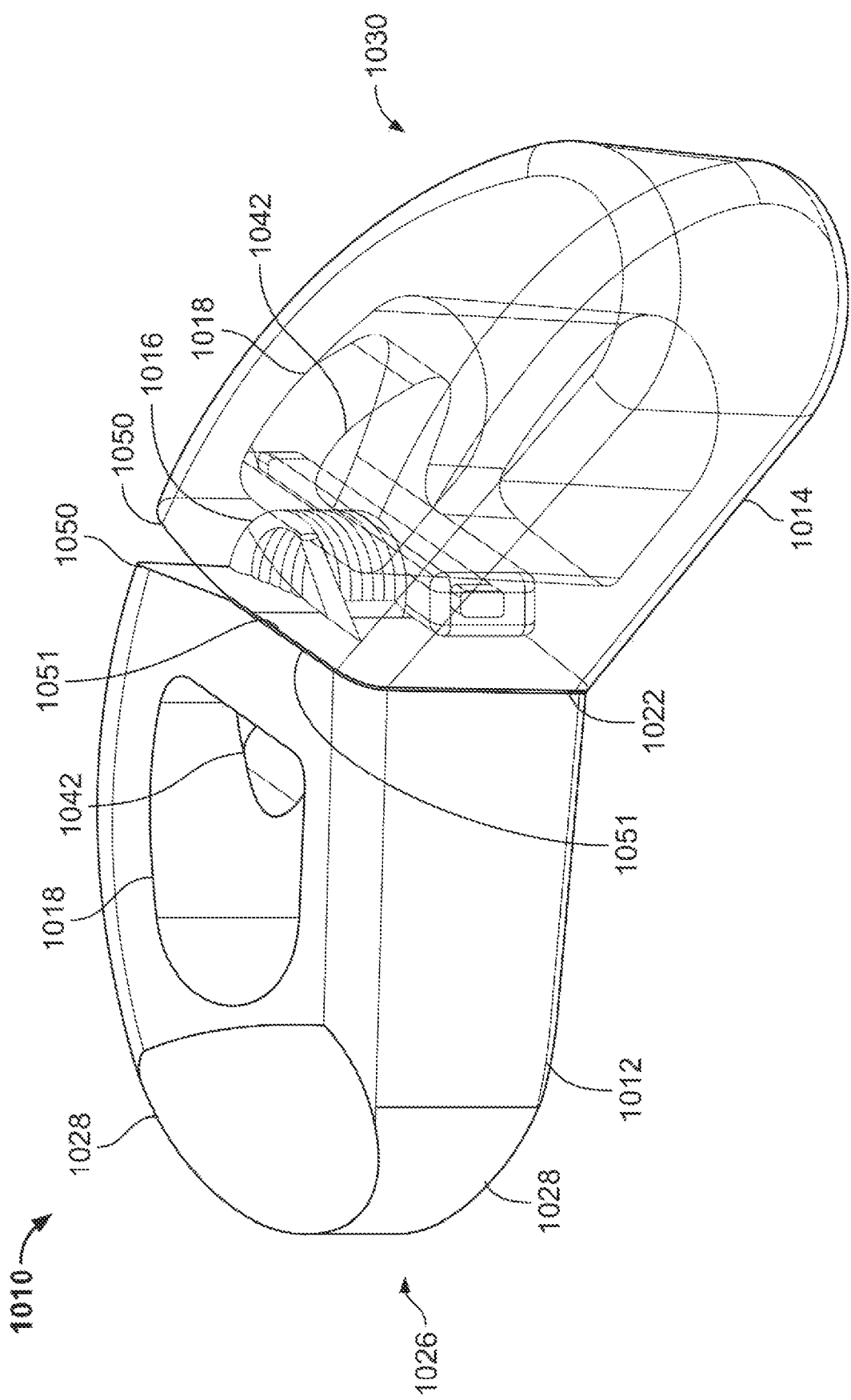
FIG. 10A is an oblique perspective view illustrating a cage according to a tenth arrangement.
Figure 10C:
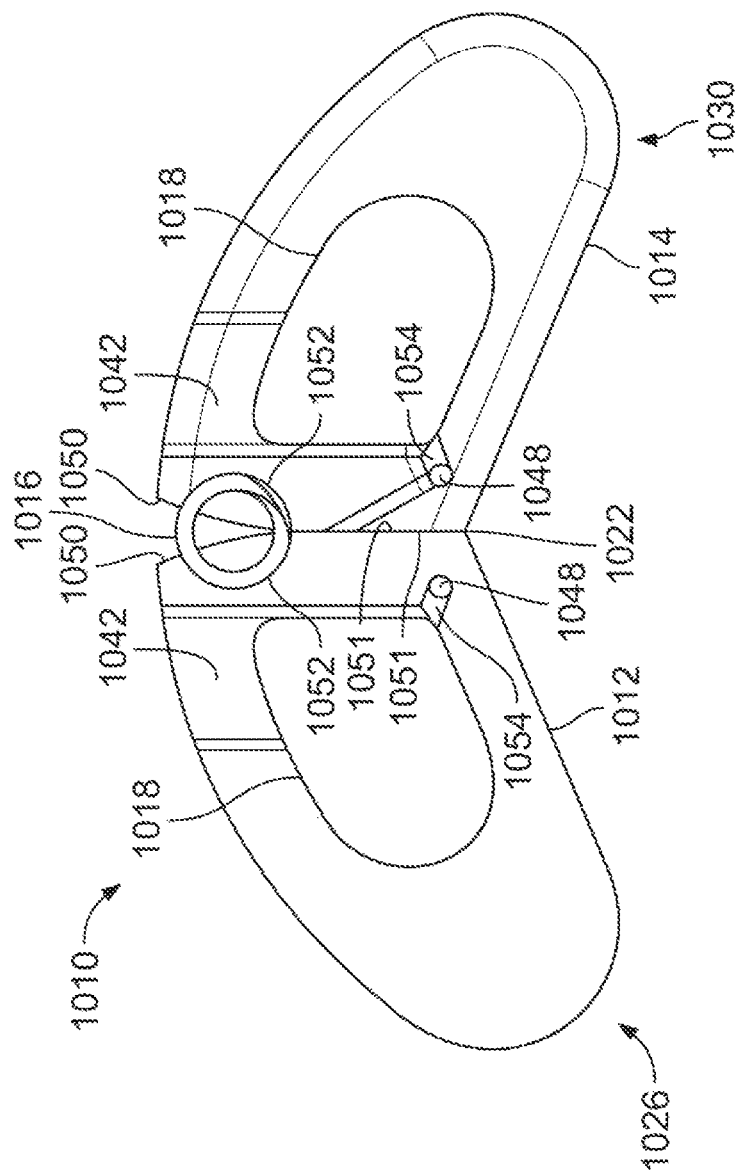
FIG. 10C is a section view taken along the transverse plane of the cage according to the tenth arrangement.
Figure 10B:
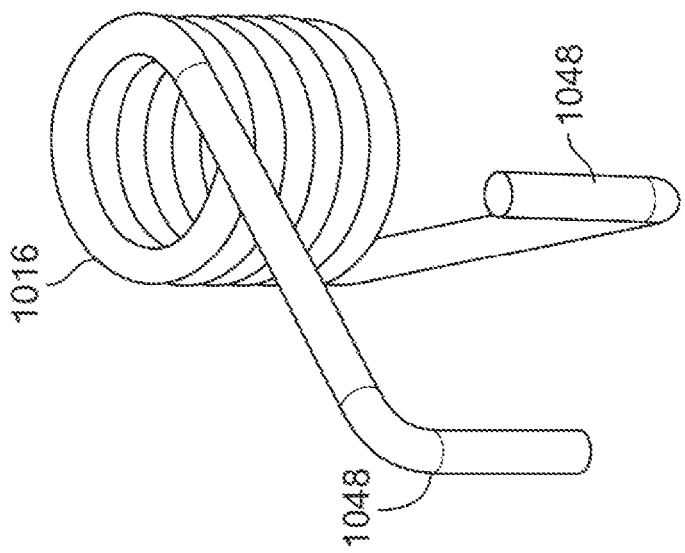
FIG. 10B is an oblique perspective view illustrating a coil spring of the cage according to the tenth arrangement.

FIG. 10A illustrates an arrangement of cage 1010 having an axial coil spring 1016, illustrated in FIG. 10B, connecting wings 1012, 1014, with proximal wing 1014 illustrated as partially transparent to show coil spring 1016 situated at a radially outer end of seam 1022. Wings 1012, 1014 are not connected except by coil spring 1016. Absent coil spring 1016, wings 1012, 1014 would therefore be freely separable. Circumferential faces of wings 1012, 1014 that meet at seam 1022 have reliefs 1050 (e.g., chamfers or fillets) at respective radially outer edges, defining an outer facet or relief 1050 and an inner facet 1051 on each of the wings 1012, 1014. Reliefs 1050 enable wings 1012, 1014 to pivot relative to one another about coil spring 1016 by allowing one wing to rock along the other such that a contact point between wings 1012, 1014 moves radially outward from the inner facets 1051 to the outer facets 1050 as coil spring 1016 is flexed. Ports 1042 extend radially outward from through holes 1018 to radially outer faces of wings 1012, 1014, so as to promote bone in-growth and/or dispersion of bone growth promoting material (e.g., autologous and/or allogeneic bone graft, a bone growth enabling matrix, and/or bone growth stimulating substances) out of the cage 1010 through the ports 1042.

As shown in FIG. 10B, coil spring 1016 includes two "L" shaped arms 1048 extending tangentially from opposite ends of the coil and axially toward each other. FIG. 10C is an axial cross section at an axial midline of cage 1010 with proximal wing 1014 illustrated as partially transparent. FIG. 10C illustrates that coil spring 1016 is disposed within arcuate channels 1052 extending axially through wings 1012, 1014 near relief 1050. Arms 1048 extend into grooves 1054 extending through wings 1012, 1014 such that positions of wings 1012, 1014 relative to one another correspond directly to a degree of flexure of coil spring 1016.

Figures 11A, 11B:
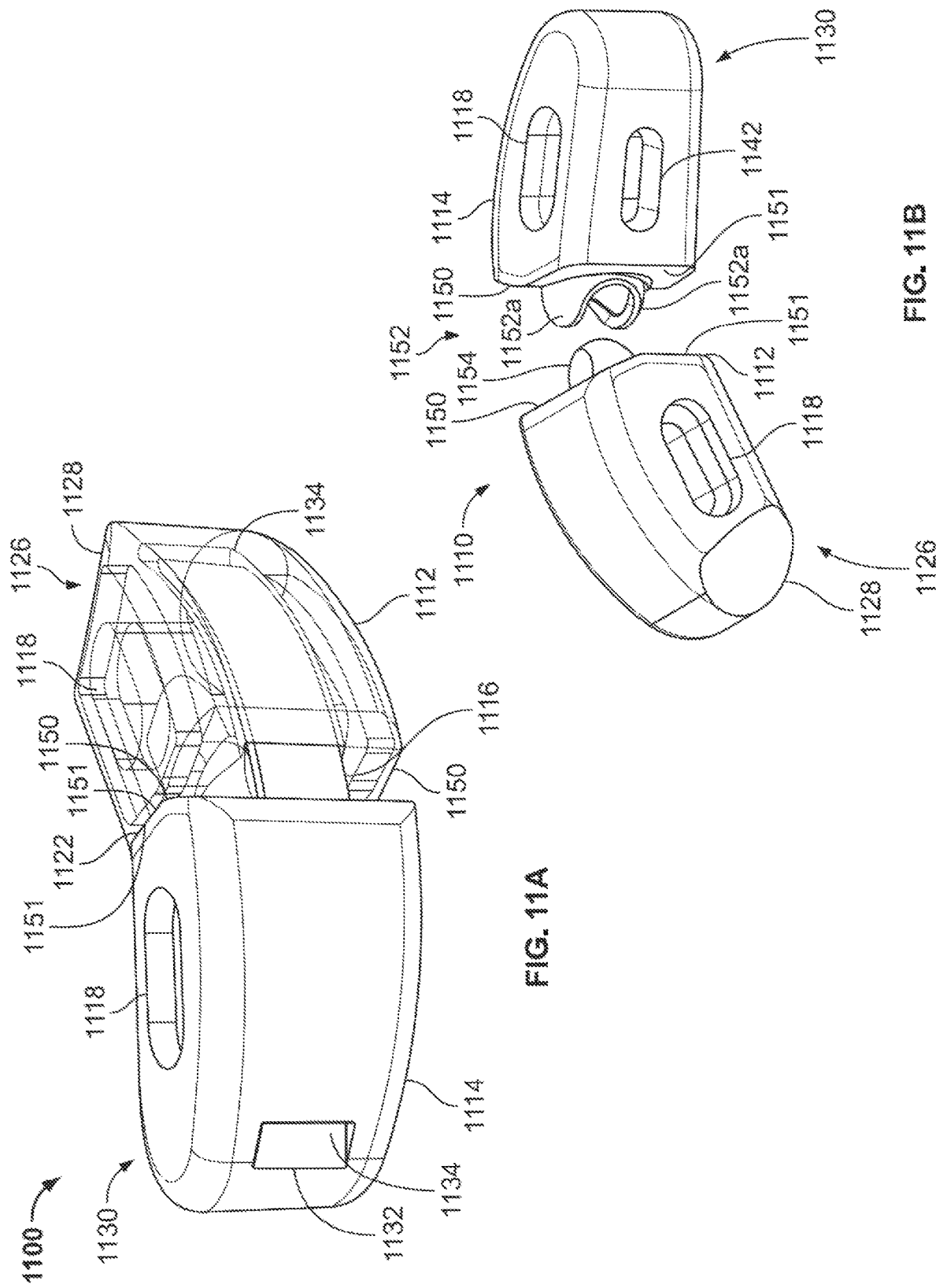
FIG. 11A is an oblique perspective view illustrating a cage according to an eleventh arrangement.
FIG. 11B is an oblique perspective view illustrating the cage according to the eleventh arrangement in a disassembled state.

FIGS. 11A-11D illustrate a cage 1110 with wings 1112, 1114 having a leaf spring 1116 for providing flexibility and/or shape memory properties, so that the wings 1112, 1114 can be repositioned with respect to one another similarly to the other embodiments described above. Wings 1112, 1114 similarly each include an inner facet 1151 and outer facet or relief 1150, with a vertex defined therebetween upon which each wing rocks when rotated relative to the other about a pivot joint having a structure detailed below. FIG. 11A illustrates distal wing 1112 as partially transparent, showing that leaf spring 1116 is disposed along internal channels 1134 extending along circumferentially outer faces of both wings 1112, 1114.

FIG. 11B shows wings 1112, 1114 without leaf spring 1116. Distal wing 1112 includes a rounded fulcrum 1154 extending circumferentially toward proximal wing 1114, which includes a socket 1152 for fulcrum 1154 to pivot within. FIGS. 11B-11C illustrate how distal wing 1112 and proximal wing 1114 may be assembled. Distal wing 1112 and proximal wing 1114 are brought together such that fulcrum 1154 approaches socket 1152, with distal wing 1112 and proximal wing 1114 about 90° out of alignment. Fulcrum 114 extends from distal wing 1112 along a fulcrum axis, and has a partially cylindrical or partially spherical shape having a thickness defined between two flat sides and corresponding to a radial direction relative to distal wing 1112 and a diameter defined perpendicular to the thickness. Fulcrum 1154 is inserted into socket 1152, and wings 1112, 1114 are rotated into alignment. Alignment is achieved by rotation of wings 1112, 1114 relative to one another such that fulcrum 1154 turns within socket 1152 about the fulcrum axis until channels 134 in wings 1112, 1114 are aligned. Fulcrum 1154 is keyed to socket 1152 such that fulcrum 1154 cannot be pulled free of socket 1152 when wings 1112, 1114 are in alignment. In the illustrated embodiment, keying of fulcrum 1154 is achieved by tabs 1152a extending to partially enclose socket 1152 such that an opening into socket 1152 defined between tabs 1152a has a width in the axial direction that is less than the diameter of fulcrum 1154 and a width in the radial direction that is greater than the diameter of fulcrum 1154. Fulcrum 1154 is thereby insertable into socket 1152 when distal wing 1112 is rotated such that an axial direction relative to distal wing 1112 is aligned with a radial direction relative to proximal wing 1114, but fulcrum 1154 is not insertable into or removable from socket 1152 when axial directions relative to both wings 1112, 1114 are aligned. When wings 1112, 1114 are aligned and fulcrum 1154 is disposed within socket 1152, fulcrum 1154 is engaged against interior surfaces of tabs 1152a to prevent withdrawal of fulcrum 1154 along the fulcrum axis.

Wings 1112, 1114 are unconnected except by keying fulcrum 1154 into socket 1152 and leaf spring 1116. Wings 1112, 1114 would therefore become freely separable absent leaf spring 1116 by rotating wings 1112, 1114 relative to one another to un-key fulcrum 1154 within socket 1152.

Figure 11D:
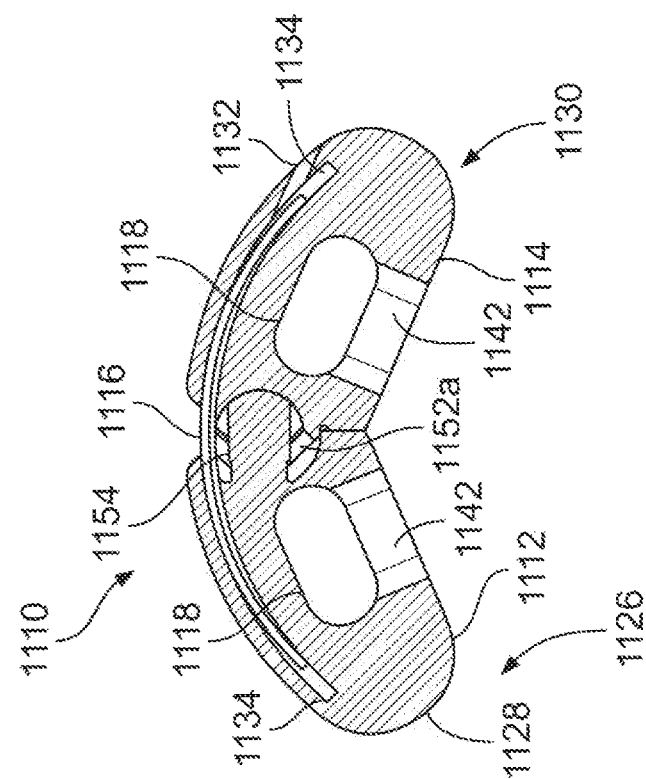
FIGS. 11C-11D are section views taken along the transverse plane of the cage according to the eleventh arrangement in, respectively, lesser and greater degrees of assembly.
Figure 11C:
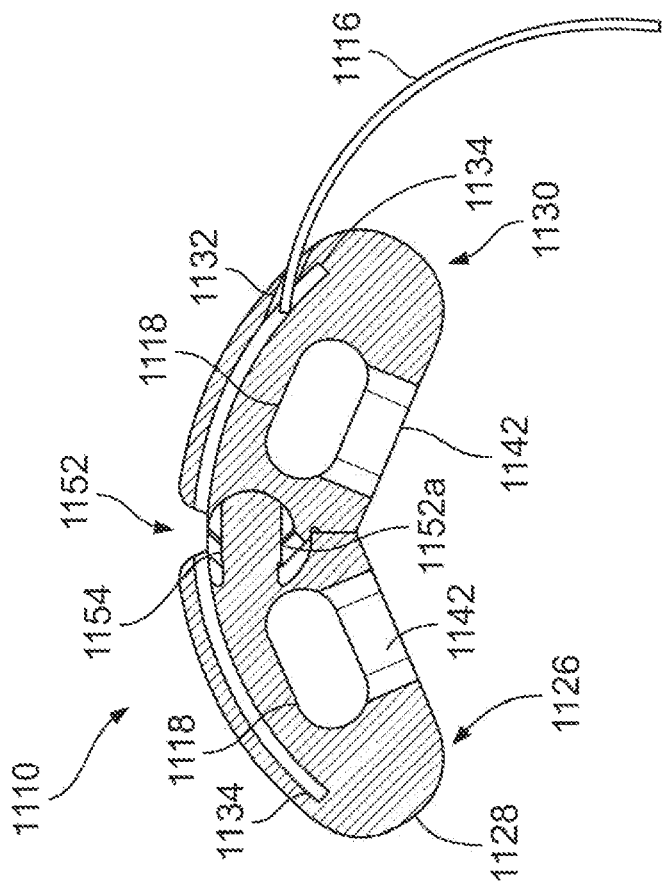

FIGS. 11C and 11D are axial cross sections at an axial midline of cage 1110. As shown, leaf spring 1116 is insertable through a slot 1132 in proximal wing 1114 located on a circumferentially outer side of proximal wing 1114 near proximal end 1130. Leaf spring 1116 deforms during passage through slot 1132 and conforms to channels 1134 upon full insertion. After assembly of cage 1110 by insertion of leaf spring 1116, positions of wings 1112, 1114 relative to one another correspond directly to a degree of flexure of leaf spring 1116. Rotation of wings 1112, 1114 out of alignment as shown in FIG. 11B is impossible after leaf spring 1116 is in place, so insertion of leaf spring 1116 holds wings 1112, 1114 together and prevents disassembly of cage 1110.

Referring now to FIGS. 12A-12C, there is depicted an exemplary method of deploying cage 1210, which may be a cage according to any of the above described arrangements, through an inserter tube 1270 into disc space 1262. The inserter tube 1270 may extend through an annulus fibrosus 1265 of the disc between two vertebrae 1264 of the spine 1261 by performing an annulotomy through the annulus 1265. The through holes of cage 1210 may be filled with morselized bone graft material prior to inserting cage 1210 into inserter tube 1270. A suture 1263 may be secured to cage 1210, for example by looping suture 1263 around features such as pin 135 within notch 134 described with regard to FIGS. 1A and 1B, or by threading suture 1263 through a hitch provided by notch 134 and pin 135, prior to insertion in inserter tube 1270. Suture 1263 shown in FIGS. 12A-12C is disposed through a groove of a deployment shaft 1272 (such as one of the bullnose instruments disclosed in the '082 patent, incorporated above), and deployment shaft 1272 is then inserted into inserter tube 1270, pushing the cage 1210 into place as deployment shaft 1272 advances distally through inserter tube 1270. The distal end of the inserter tube 1270 may have a curved portion 1274 to help guide deployment of the cage 1210 as it advances out of the tube 1270. The deployment shaft 1272 may include a blunt distal tip 1260 that can project out of the distal end of the inserter tube 1270 to aid in distracting or maintaining the distraction of the disc space 1262. Once properly positioned, radiographical techniques may be used to verify the positioning of cage 1210, whereupon suture 1263 is removed, as is deployment shaft 1272. Inserter tube 1270 may remain in place in disc space 1262 for application of bone graft material before inserter tube 1270 is removed.

Insertion of cage 1210 through insertion tube 1270 limits displacement of patient tissue to a cross-sectional area of insertion tube 1270. This is a potential improvement over insertion of cage 1210 in cage's 1210 resting shape, as cage's 1210 irregular resting shape creates a potential for displacing patient tissue across a greater area than that of a cross-section of cage 1210 at any given location. Cage 1210 must be deformed from its resting shape to fit in insertion tube 1270 as shown in FIG. 12A, and elastically returns to its resting shape upon exiting insertion tube 1270 as shown in FIGS. 12B-12C. Deformation of cage 1210 shown in FIG. 12A is accomplished by flexure of bridge 1216 of cage 1210 such that wings 1212, 1214 spread apart and bridge 1216 presses flat against an interior surface of inserter tube 1270. Cage 1210 returns to its resting shape by bridge 1216 bowing to an arcuate shape and bringing wings 1212, 1214 together. Bridge's 1216 capacity for elastic deformation is therefore conducive to delivery of a cage 1210 that has an irregular resting shape, while causing relatively little displacement of patient tissue when advancing the cage 1210 towards the spine 1.

In addition to the insertion method described above with regard to FIGS. 12A-12C, any method of insertion described with regard to interbody implants described in the '082 patent, incorporated above, may be employed for insertion of any of the cages described within the present disclosure.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A lumbar interbody fusion device, comprising:
   a first wing and a second wing separated by a seam; and
   a bridge monolithically formed with the first and second wings extending along a path from the first wing to the second wing, wherein the bridge includes a coil defining a cavity therein, the cavity extending circumferentially along the path of the bridge, and
   wherein a cavity extends through the bridge along the path from the first wing to the second wing.

2. The device of claim 1, wherein the coil is defined by a spiral slot extending circumferentially along the bridge.

3. The device of claim 2, wherein a first end of the spiral slot ends in a first circular node on an outer surface of the bridge and a second end of the spiral slot ends in a second circular node on the outer surface of the bridge.

4. The device of claim 3, wherein the first node and the second node have a diameter greater than a width of the slot.

5. The device of claim 1, wherein the first and second wings define a first opening between a superior end of the device and the coil, and the first and second wings define a second opening between an inferior end of the device and the coil.

6. The device of claim 1, wherein the first wing includes a first port extending from an interior surface of the first wing to a first hole, and the second wing includes a second port extending from an interior surface of the second wing to a second hole.

7. The device of claim 1, wherein the first wing includes a threaded bore extending distally from a concavity defined in a proximal end of the device, wherein the threaded bore is configured to connect to a delivery tool.

8. The device of claim 1, wherein the bridge has an arcuate resting shape centered on an axis extending perpendicular to a radial direction of the arcuate resting shape, the axis extending from an inferior direction to a superior direction, and the wings being radially inward of the bridge in the radial direction.

9. A lumbar interbody fusion device, comprising:
   a first wing and a second wing entirely separated by a seam, wherein the seam is formed from a recess of the first wing that is concave in a direction towards the second wing, and a projection of the second wing is convex in a direction towards the first wing, wherein the recess is configured to receive the projection; and
   a bridge extending along a path from the first wing to the second wing.

10. The device of claim 9, wherein the recess and projection are both "V" shaped.

11. The device of claims 10, wherein the projection extends into the recess to define a chevron shape of the seam.

12. The device of claim 9, wherein the first wing includes a first port extending from an interior surface of the first wing to a first hole, and the second wing includes a second port extending from an interior surface of the second wing to a second hole.

13. The device of claim 9, wherein the first wing includes a threaded bore extending distally from a concavity defined in a proximal end of the device, wherein the threaded bore is configured to connect to a delivery tool.

14. The device of claim 9, wherein the bridge has an arcuate resting shape centered on an axis extending perpendicular to a radial direction of the arcuate resting shape, the axis extending from an inferior direction to a superior direction, and the wings being radially inward of the bridge in the radial direction.

15. The device of claim 9, wherein a cavity extends through the bridge along the path from the first wing to the second wing.

16. The device of claim 9, wherein the bridge is monolithically formed with the first and second wings.

17. A method of manufacturing the fusion device of claim 9, comprising:
   additively manufacturing the device by stacking layers in a vertical orientation.

18. The method of claim 17, wherein the layers are layers of titanium.

* * * * *